(12) United States Patent
Freeman et al.

(10) Patent No.: US 9,486,521 B2
(45) Date of Patent: Nov. 8, 2016

(54) THERAPEUTIC APPLICATIONS TARGETING SARM1

(71) Applicants: UNIVERSITY OF MASSACHUSETTS, Shrewsbury, MA (US); UNIVERSITY OF MIAMI, Miami, FL (US)

(72) Inventors: Marc Freeman, Barre, MA (US); Stephan Zuchner, Pinecrest, FL (US)

(73) Assignees: University of Massachusetts, Boston, MA (US); University of Miami, Miami, FL (US)

( * ) Notice: Subject to any disclaimer, the term of this patent is extended or adjusted under 35 U.S.C. 154(b) by 0 days.

(21) Appl. No.: 14/087,206

(22) Filed: Nov. 22, 2013

(65) Prior Publication Data

US 2014/0079712 A1   Mar. 20, 2014

Related U.S. Application Data

(62) Division of application No. 13/530,998, filed on Jun. 22, 2012, now abandoned.

(60) Provisional application No. 61/501,111, filed on Jun. 24, 2011.

(51) Int. Cl.

| | |
|---|---|
| *A61K 31/713* | (2006.01) |
| *A61K 31/7088* | (2006.01) |
| *G01N 33/68* | (2006.01) |
| *G01N 33/50* | (2006.01) |
| *A61K 38/00* | (2006.01) |
| *A61K 39/395* | (2006.01) |
| *G01N 33/566* | (2006.01) |

(52) U.S. Cl.
CPC ....... *A61K 39/3955* (2013.01); *A61K 31/7088* (2013.01); *A61K 31/713* (2013.01); *A61K 38/00* (2013.01); *G01N 33/5058* (2013.01); *G01N 33/566* (2013.01); *G01N 33/6896* (2013.01); *G01N 2500/04* (2013.01); *G01N 2800/2814* (2013.01); *G01N 2800/2835* (2013.01)

(58) Field of Classification Search
CPC ........... A61K 31/7088; A61K 31/713; A61K 38/00; A61K 39/3955
See application file for complete search history.

(56) References Cited

U.S. PATENT DOCUMENTS

2004/0087642 A1* 5/2004 Zeldis et al. ................. 514/406
2007/0142366 A1* 6/2007 Graczyk et al. ........... 514/225.2

OTHER PUBLICATIONS

Resnick 2004 "targeting JNK3 for the treatment of neurodegenerative disorders" DDT 9(21):932-939.*
Wakabayashi 2010 "Involvement of the peripheral nervous system in synucleinopathies, tauopathies and other neurodegenerative proteinopathies of the brain" Acta Neuropathol 120:1-12.*
International Search Report and Written Opinion in International Application No. PCT/US2012/043768, dated Jan. 29, 2013, 12 pages.
Arroyo et al., "Toll-like receptors are key players in neurodegeneration," *Intn'l Immunopharma.*, 2011, 11(10):1415-1421.
Ataman et al., "Rapid Activity-Dependent Modifications in Synaptic Structure and Function Require Bidirectional Wnt Signaling," *Neuron*, 2008, 57:705.

(Continued)

*Primary Examiner* — Adam M Weidner
(74) *Attorney, Agent, or Firm* — Fish & Richardson P.C.

(57) ABSTRACT

The present disclosure provides methods for reducing axonal and/or synaptic degradation in neurons by modulating sterile α/Armadillo/Toll-Interleukin receptor homology domain protein (SARM) activity and/or expression.

10 Claims, 17 Drawing Sheets
(1 of 17 Drawing Sheet(s) Filed in Color)

(56) References Cited

OTHER PUBLICATIONS

Avery et al., "Wld$^S$ requires Nmnat1 enzymatic activity and N16-VCP interactions to suppress Wallerian degeneration," *J Cell Biol*, 2009, 184(4):501-513.
Barrientos et al., "Axonal Degeneration is Mediated by the Mitochondrial Permeability Transition Pore," *J Neurosci*, 2011, 31:966.
Belinda et al., "SARM: a novel Toll-like receptor adaptor, is functionally conserved from arthropod to human," *Mole. Immunol.*, 2007, 45:1732-1742.
Broadus et al., "Staufen-dependent localization of *prospero* mRNA contributes to neuroblast daughter-cell fate," *Nature*, 1998, 391:792.
Buss et al., "Adaptive roles of Programmed Cell Death during Nervous System Development," *Annul Rev Neurosci*, 2006, 29:1-35.
Carty et al., "The human adaptor SARM negatively regulates adaptor protein TRIF-dependent Toll-like receptor signaling," *Nature Immunology*, 2006, 7:1074-1081.
Chang et al., "Microtubule-based localization of a synaptic calcium-signaling complex is required for left-right neuronal asymmetry in *C. elegans*," *Development*, 2011, 138:3509-3518.
Chen et al., "Sarm1, a negative regulator of innate immunity, interacts with syndecan-2 and regulates neuronal morphology," *J. Cell Biol.*, 2011, 193:769-784.
Chuang and Bargmann, "A Toll-interleukin 1 repeat protein at the synapse specifies asymmetric odorant receptor expression via ASK1 MAPKKK signaling," *Genes Dev*, 2005, 19:270-281.
Coleman and Freeman, "Wallerian Degeneration, Wld$^S$, and Nmnat," *Annu Rev Neurosci*, 2010, 33:245-267.
Coleman and Perry, "Axon pathology in neurological disease: a neglected therapeutic target," *Trends Neurosci*, 2002, 25:532-237.
Dalod, "Studies of SARM1 Uncover Similarities between Immune and Neuronal Responses to Danger," *Science Signaling*, 2007, 417:1-3.
Deckwerth and Johnson, Jr., "Neurites can remain viable after destruction of the Neuronal Soma by Programmed Cell Death (Apoptosis)," *Dev Biol*, 1994,_ 165:63-72.
Famakin et al., "Disruption of downstream MyD88 or TRIF Toll-like receptor signaling does not protect against cerebral ischemia," *Brain Research*, 2011, 1388:148-156 (author manuscript).
Finn et al., "Evidence that Wallerian Degeneration and Localized Axon Degeneration Induced by Local Neurotrophin Deprivation Do Not Involve Caspases," *J Neurosci*, 2000, 20:1333-1341.
George et al., "Axotomy-induced axonal degeneration is mediated by calcium influx through ion-specific channels," *J Neurosci*, 1995, 15:6445-6452.
Gilley and Coleman, "Endogenous Nmnat2 is an Essential Survival Factor for Maintenance of Healthy Axons," *PLoS Biol*, 2010, 8(1):1-18.
Glass et al., "Prolonged survival of transected nerve fibres in C57BL/Ola mice is an intrinsic characteristic of the axon," *J Neurocytol*, 1993, 22:311-321.
Grether et al., "The *head* involution *defective* gene of Drosophila *melanogaster* functions in programmed cell death," *Genes Dev*, 1995, 9:1694-1708.
Hoopfer et al., "Wld$^S$ Protection Distinguishes Axon Degeneration following Injury from Naturally Occurring Development Pruning," *Neuron*, 2006, 50:883-895.
Kim et al., "Distinctive role of MyD88 (SARM) in neurodegeneration and host defense," Abstract form the Toll2008 meeting conducted in Lisbon, Portugal from Sep. 24-27, 2008, 1 page.
Kim et al., "MyD88-5 links mitochondria, microtubules, and JNK3 in neurons and regulates neuronal survival," *JEM*, 2007, 204:2063-2074.
Klein, "Immunolabeling of Imaginal Discs," *Methods Mol Biol*, 2008, 420:253-263.
Lee and Luo, "Mosaic analysis with a repressible cell marker (MARCM) for Dropsophila neural development," *Trends Neurosci*, 2001, 24:251-254.
Li et al., "Interactive Sites in the MyD88 Toll/Interleukin (IL) 1 Receptor Domain Responsible for Coupling to the IL1β Signaling Pathway," *The Journal of Biological Chemistry*, 2005, 280:26152-26159.
Lunn, et al., "Absence of Wallerian Degeneration does not Hinder Regeneration in Peripheral Nerve," *Eur J Neurosci*, 1989, 1(1):27-33.
Luo and O'Leary, "Axon retraction and degeneration in development and disease," *Annu Rev Neurosci*, 2005, 28:127-149.
MacDonald et al., "The *Drosophila* Cell Corpse Engulfment Receptor Draper Mediates Glial Clearance of Severed Axons," *Neuron* 2006, 50:869-881.
MacInnis and Campenot, "Regulation of Wallerian degeneration and nerve growth factor withdrawal-induced pruning of axons of sympathetic neurons by the proteasome and the MEK/Erk pathway," *Mol Cell Neurosci*, 2005, 28:430-439.
Miguel-Aliaga, and Thor, "Segment-specific prevention of pioneer neuron apoptosis by cell-autonomous, postmitotic Hox gene activity," *Development*, 2004, 131:6093.
Miller et al., "A DLK-dependent axon self-destruction program promotes Wallerian degeneration," *Nat Neurosci.*, 2009, 12:387-389.
Mink et al., "A Novel Human Gene (SARM) at Chromosome 17q11 Encodes a Proteign with a SAM Motif and Structural Similarity to Armadillo/β-Catenin That is Conserved in Mouse, Drosophila, and Caenorhabditis elegans," *Genomics*, 2001, 74:234-244.
Monuki et al., "Mechanisms of cerebral cortical patterning in mice and humans," *Nat Neurosci*, 2001, 4:1199-1206.
Nikolaev et al., "APP binds DR6 to trigger axon pruning and neuron death via distinct caspases," *Nature*, 2009, 457:981-989.
O'Neil et al., "The Toll-IL-1 receptor adaptor family grows to five members," *Trends Immunol*, 2003, 24:286-290.
Peng et al., "SARM inhibits both TRIF- and MyD88-mediated AP-1 activation," *Eur. J. Immunol*, 2010, 40(6):1738-47.
Raff et al., "Axonal Self-Destruction and Neurodegeneration," *Science*, 2002, 296:868-871.
Resnick et al, "Targeting JNK3 for the treatment of neurodegenerative disorders," *DDT*, 2004, 9:932-939.
Simonin et al., "The neuroprotective effects of the Wld$^S$ gene are correlated with proteasome expression rather than apoptosis," *Eur. J. Neurosci*, 2007, 25:2269-2274.
Vosshall et al., "A Spatial map of Olfactory Receptor Expression in the *Drosophila* Antenna," *Cell*, 1999, 96:725.
Waller, "Experiments on the Section of the Glossopharyngeal and Hypoglassal Nerves of the Frog, and observations of the alterations thereby in the Structure of their Primitive Fibres," *Philos. Trans. R. Soc. Lond. B Biol. Sci.Pt II*, 1850, 140:423-429.
Whitmore et al., "The proapoptotic proteins Bax and Bak are not involved in Wallerian degeneration," *Cell Death Differ*, 2003, 10:260-261.
Yuan et al., "Amphioxus SARM Involved in Neural Development May Function as a Suppressor of TLR Signaling," *J. Immunol*, 2010, 184:6874-6881.
Zhai et al., "Involvement of the Ubiquitin-Proteasome System in the Early Stages of Wallerian Degeneration," *Neuron*, 2003, 39:217.
Simin Baharlou, "Notification Concerning Transmittal of International Preliminary Report on Patentability (Chapter I of the Patent Cooperation Treaty)", Int. Appl. No. PCT/US2012/043768, mailed on Jan. 9, 2014 (7 pages).
Coleman, Michael P., et al., "An 85-kb tandem triplication in the slow Wallerian degeneration (Wld$^S$) mouse", Proceedings of the National Academy of Sciences, vol. 95:9985-9990, 1998.
Sagot, Yves, et al., "Bcl-2 overexpression prevents motoneuron cell body loss but not axonal degeneration in a mouse model of a neurodegenerative disease", The Journal of Neuroscience, vol. 15(11):7727-7733, 1995.
Neukomm, Lukas J. and Marc R. Freeman, "Diverse cellular and molecular modes of axon degeneration", Trends in cell biology, vol. 24(9):515-523, 2014.

* cited by examiner

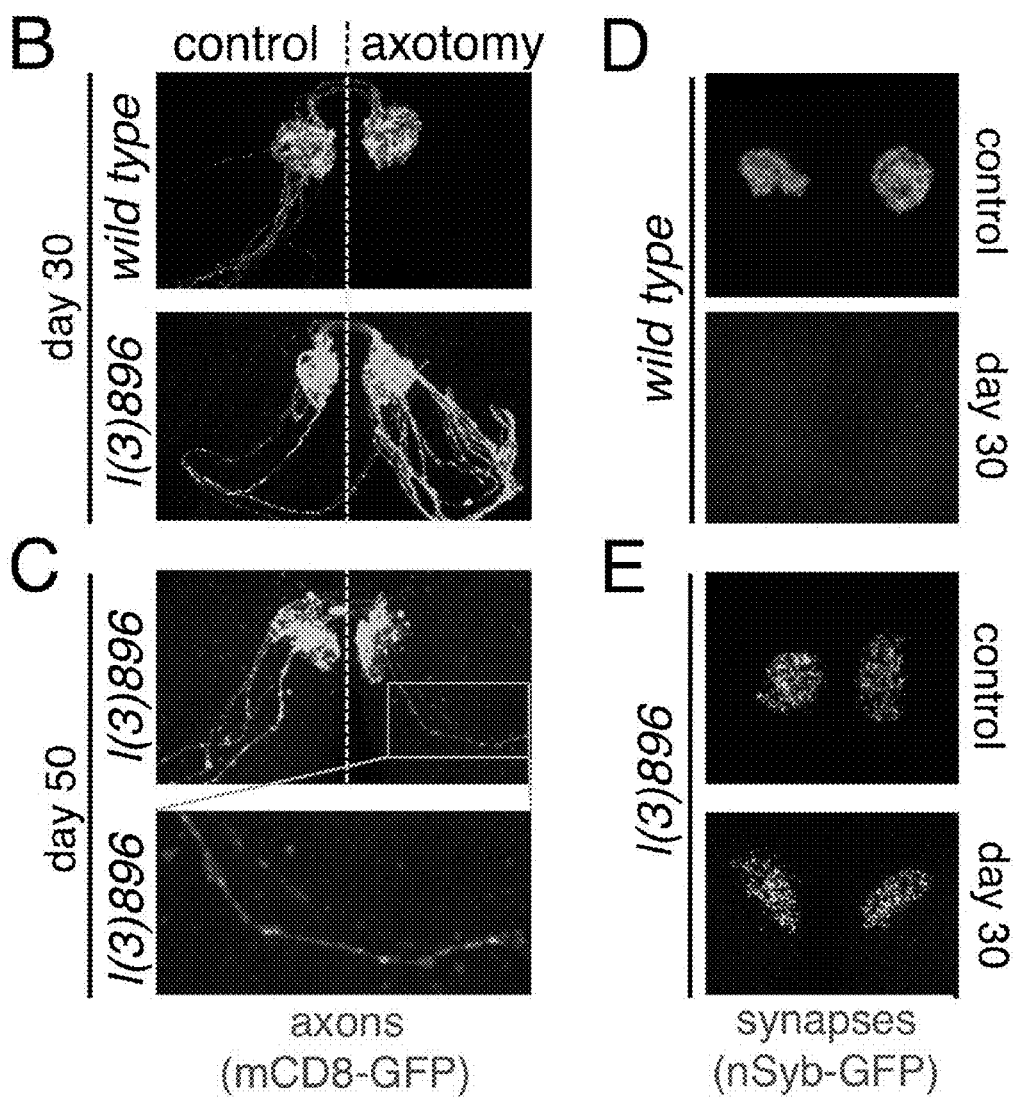
FIGs. 1B-E

| mutant line | genomic location of lesion | original nucleotide | new nucleotide | resulting protein change |
|---|---|---|---|---|
| *l(3)896* | 8,096,399 | C | T | Q603Stop |
| *l(3)4621* | 8,092,275 | C | A | D347E |
| *l(3)4621* | 8,097,436 | G | A | W949Stop |
| *l(3)4705* | 8,096,632 | C | T | Q681Stop |

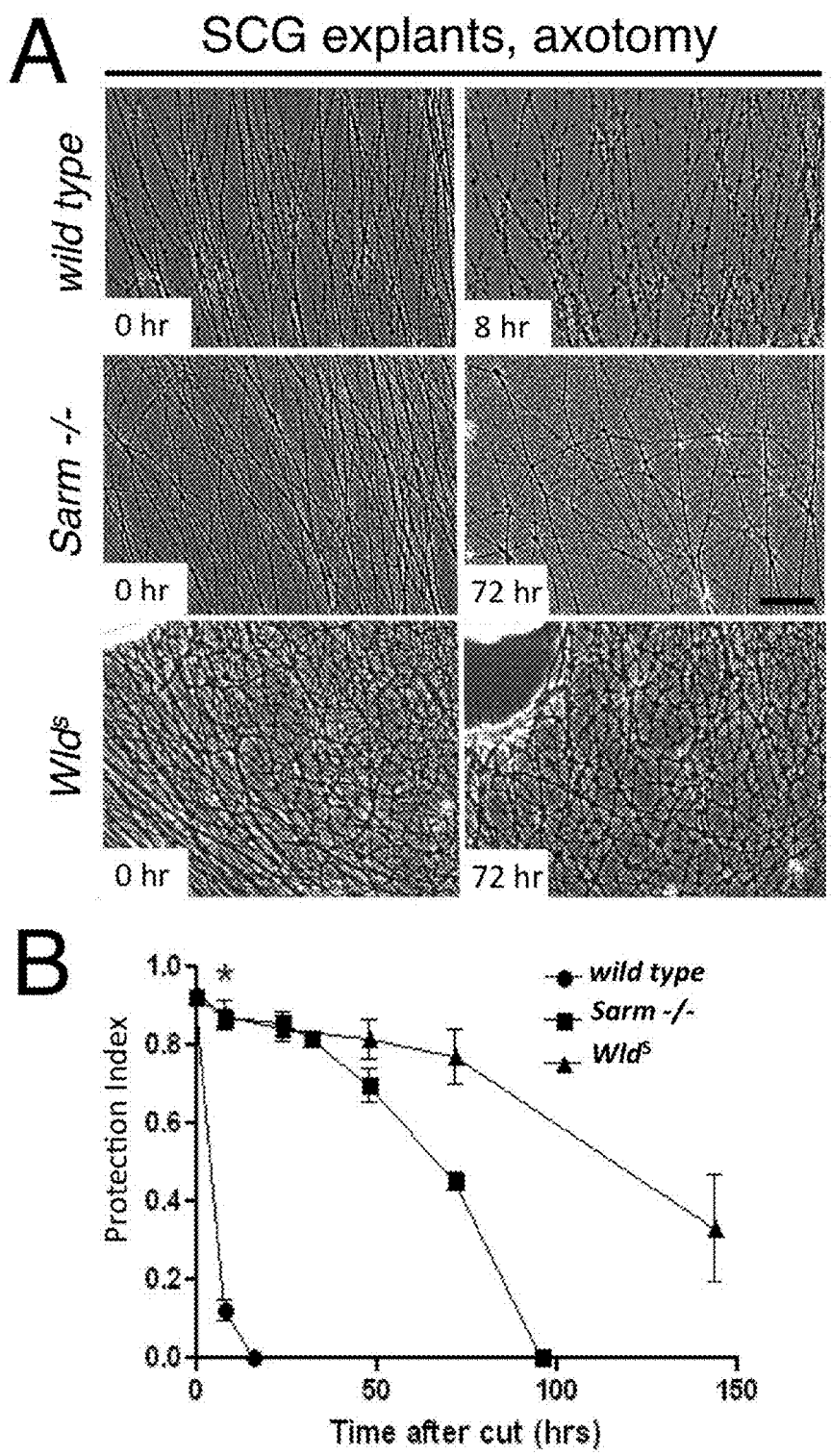
FIGs. 3A-B

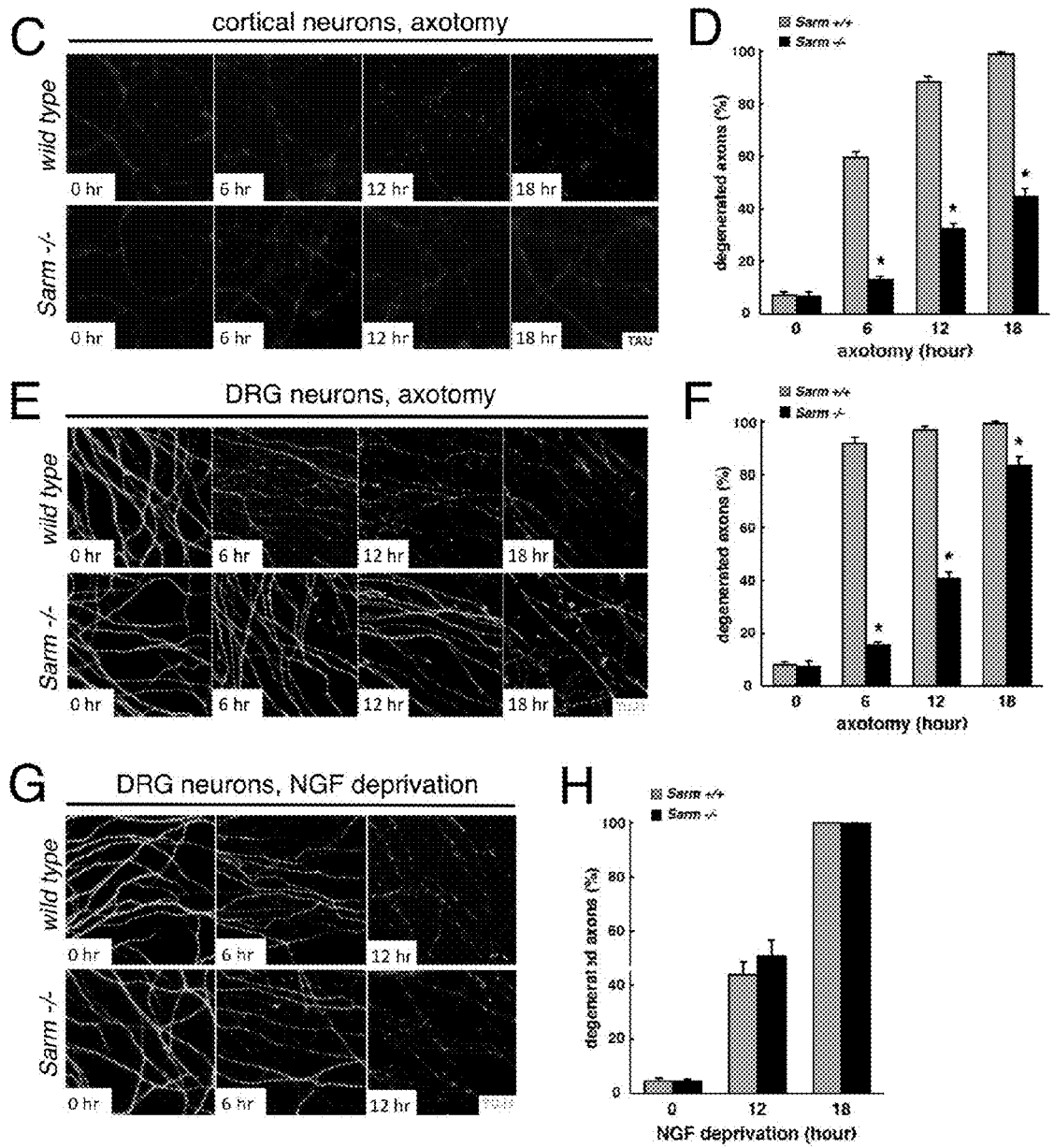
FIGs. 3C-H

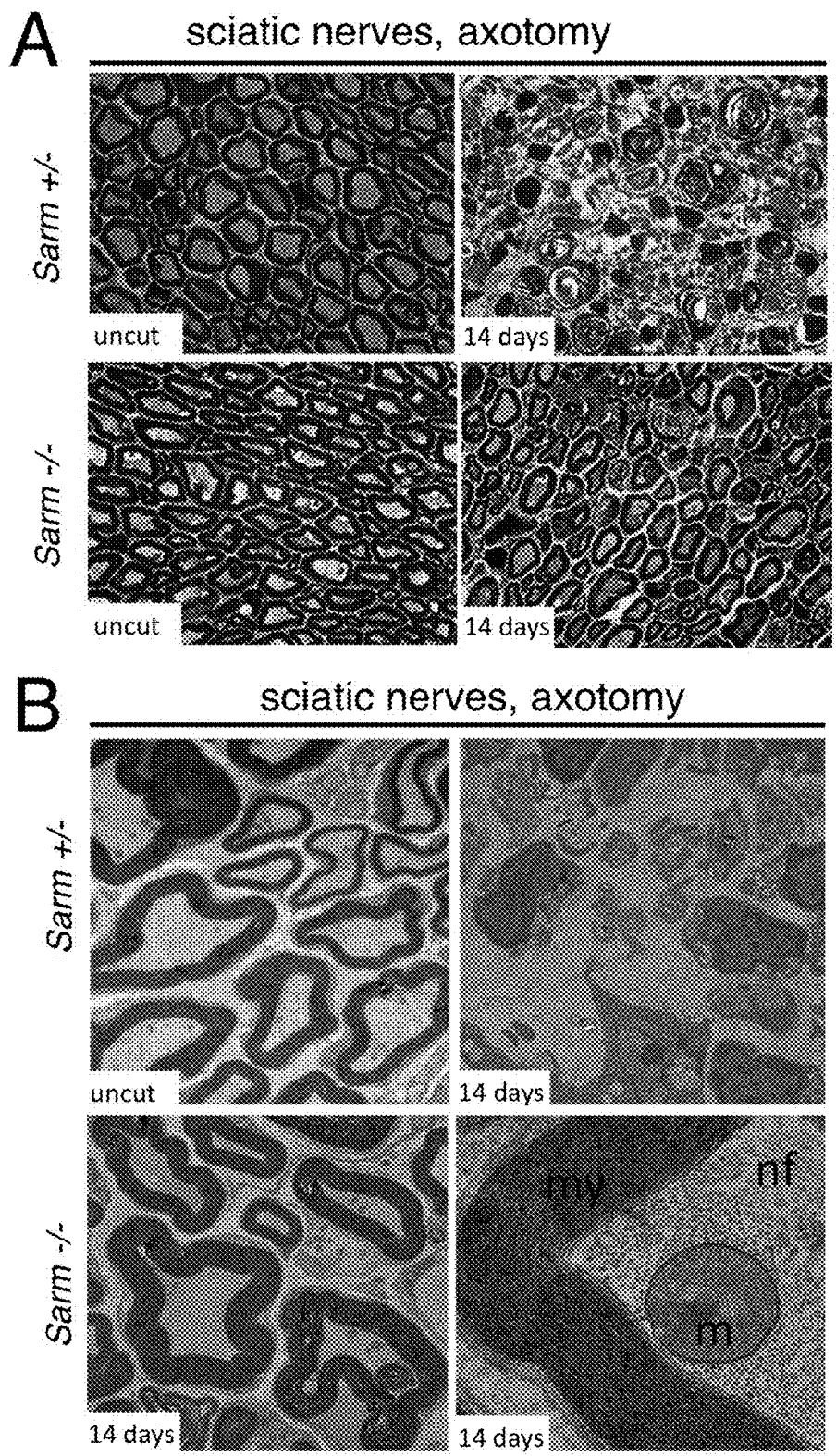
FIGs. 4A-B

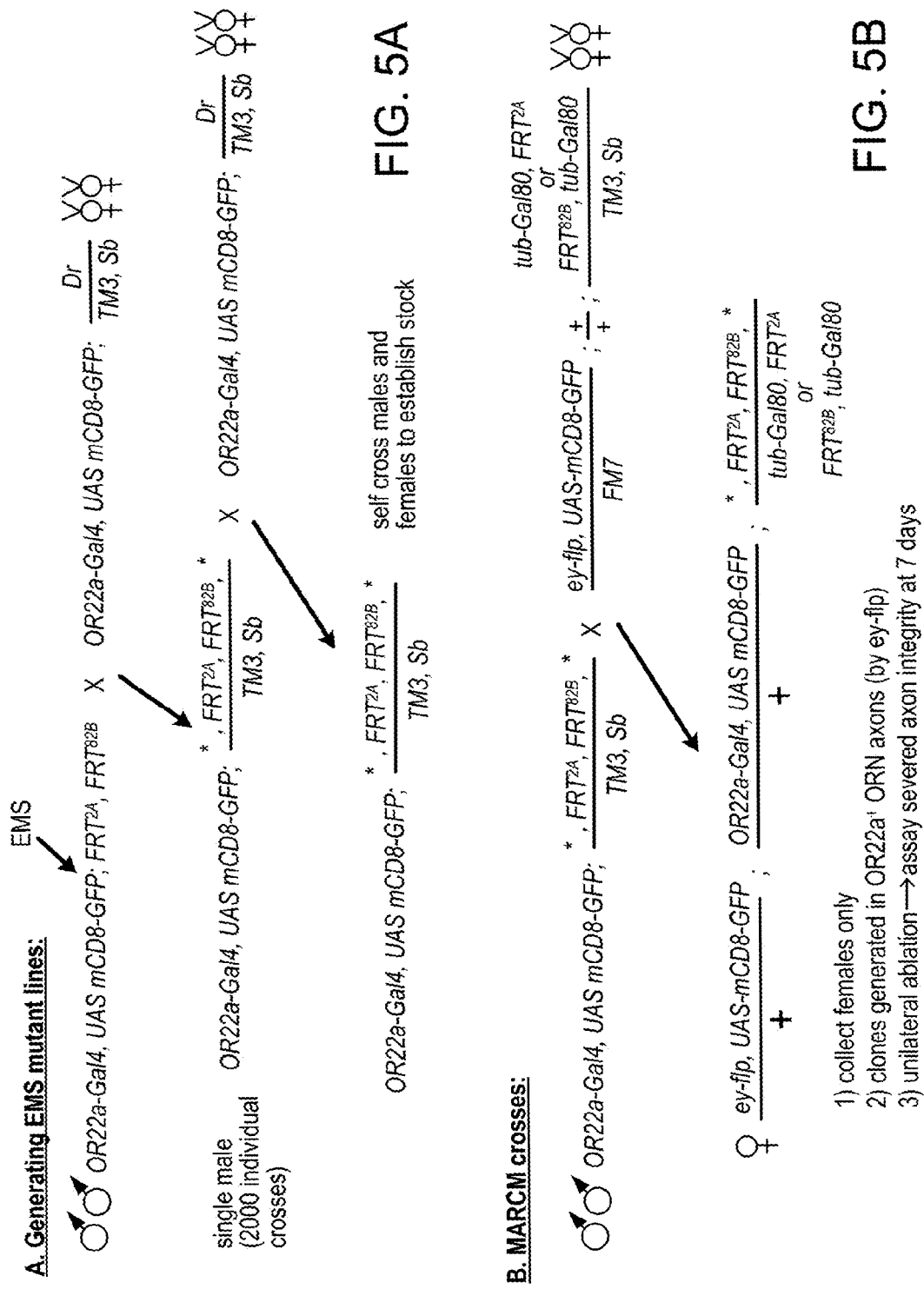

ized that peripheral neuropathy, brain injury, and neurodegenerative disease.

SEQUENCE LISTING

```
<160> NUMBER OF SEQ ID NOS: 10

<210> SEQ ID NO 1
<211> LENGTH: 7001
<212> TYPE: DNA
<213> ORGANISM: Homo sapiens
<300> PUBLICATION INFORMATION:
<308> DATABASE ACCESSION NUMBER: GenBank Accession No. NM_015077

<400> SEQUENCE: 1
ccaaaacccg ggtctctccg cgtggccccg cctccaggcc ggggatgtcc cccgcggccc      60
cgcgcccatg gtcctgacgc tgcttctctc cgcctacaag ctgtgtcgct tcttcgccat     120
gtcgggccca cggccgggcg ccgagcggct ggcggtgcct gggccagatg ggggcggtgg     180
cacgggccca tggtgggctg cgggtggccg cgggccccgc gaagtgtcgc cggggcagg     240 caccgaggtg caggacgccc tggagcgcgc gctgccggag ctgcagcagg ccttgtccgc     300
gctgaagcag gcgggcggcg cgcgggccgt gggcgccggc ctggccgagg tcttccaact     360
ggtggaggag gcctggctgc tgccggccgt gggccgcgag gtagcccagg gtctgtgcga     420
cgccatccgc ctcgatggcg gcctcgacct gctgttgcgg ctgctgcagg cgccggagtt     480
ggagacgcgt gtgcaggccg cgcgcctgct ggagcagatc ctggtggctg agaaccgaga     540
ccgcgtggcg cgcattgggc tgggcgtgat cctgaacctg gcgaaggaac gcgaacccgt     600
agagctggcg cggagcgtgg caggcatctt ggagcacatg ttcaagcatt cggaggagac     660
```

-continued

```
atgccagagg ctggtggcgg ccggcggcct ggacgcggtg ctgtattggt gccgccgcac      720
ggaccccgcg ctgctgcgcc actgcgcgct ggcgctgggc aactgcgcgc tgcacggggg      780
ccaggcggtg cagcgacgca tggtagagaa gcgcgcagcc gagtggctct cccgctcgc       840
cttctccaag gaggacgagc tgcttcggct gcacgcctgc ctcgcagtag cggtgttggc      900
gactaacaag gaggtggagc gcgaggtgga gcgctcgggc acgctggcgc tcgtggagcc      960
gcttgtggcc tcgctggacc ctggccgctt cgcccgctgt ctggtggacg ccagcgacac     1020
aagccagggc cgcgggcccg acgacctgca gcgcctcgtg ccgttgctcg actctaaccg     1080
cttggaggcg cagtgcatcg ggctttccta cctctgcgcc gaggctgcca tcaagagcct     1140
gcaaggcaag accaaggtgt tcagcgacat cggcgccatc cagagcctga acgcctggt      1200
ttcctactct accaatggca ctaagtcggc gctggccaag cgcgcgctgc gcctgctggg     1260
cgaggaggtg ccacggccca tcctgccctc cgtgcccagc tggaaggagg ccgaggttca     1320
gacgtggctg cagcagatcg gtttctccaa gtactgcgag agcttccggg agcagcaggt     1380
ggatggcgac ctgcttctgc ggctcacgga ggaggaactc cagaccgacc tgggcatgaa     1440
atcgggcatc acccgcaaga ggttctttag ggagctcacg gagctcaaga ccttcgccaa     1500
ctattctacg tgcgaccgca gcaacctggc ggactggctg ggcagcctgg acccgcgctt     1560
ccgccagtac acctacggcc tggtcagctg cggcctggac cgctccctgc tgcaccgcgt     1620
gtctgagcag cagctgctgg aagactgcgg catccacctg ggcgtgcacc gcgcccgcat     1680
cctcacggcg gccagagaaa tgctacactc cccgctgccc tgtactggtg gcaaacccag     1740
tggggacact ccagatgtct tcatcagcta ccgccggaac tcaggttccc agctggccag     1800
tctcctgaag gtgcacctgc agctgcatgg cttcagtgtc ttcattgatg tggagaagct     1860
ggaagcaggc aagttcgagg acaaactcat ccagagtgtc atgggtgccc gcaactttgt     1920
gttggtgcta tcacctggag cactggacaa gtgcatgcaa gaccatgact gcaaggattg     1980
ggtgcataag gagattgtga ctgctttaag ctgcggcaag aacattgtgc ccatcattga     2040
tggcttcgag tggcctgagc cccaggtcct gcctgaggac atgcaggctg tgcttacttt     2100
caacggtatc aagtggtccc acgaatacca ggaggccacc attgagaaga tcatccgctt     2160
cctgcagggc cgctcctccc gggactcatc tgcaggctct gacaccagtt tggagggtgc     2220
tgcacccatg ggtccaacct aaccagtccc cagttcccca gccctgctgt gacttccatt     2280
tccatcgtcc tttctgaagg aacagctcct gaaaccagtc ccctgggct gagacaacct      2340
gggctcttct taggaaatgg ctctccctcc cctgtcccc caccctcatg gcccacctcc      2400
aacccacttt cctcagtatc tggagaggga agggaagtca ggcttgggca cgggaggtta     2460
gaactccccc aggccctgcc attgggttgt ctgtctccgt catggggagg gtccctgctc     2520
agttctggag acactggagt tggggtgggg gtggttctgc attcccttct cctgctgata     2580
gcagtcagct tgaggaggat gaaggaaggc agcctcagac aggaattaag gcaatgccca     2640
ggcgggcctg ggcactgtat tctgagcaaa ggcctgggcc caggagccag ccagggatga     2700
gtgccatcat ggctctccac tcagactgtg cctggcccct gcacttacaa cttcctgccg     2760
ctctgtggcc ttgccctgta atcactcagt gcccttagct agcctgacta agtcccagat     2820
ccctacagc ttccttcggt gtggtatctt ttgccacatc cagggcgagg gttgaggcaa      2880
accagccctc cctctgactt ccttgtcact gcagccagct tgctgcact tgctggtgca      2940
caggagcctc ctgtttgggc ctgggtctgg gcatggggag gccgtgcctc aaagcccacc     3000
```

```
ctaccccatg ccttggtgct gtgcctcagg ctccttcctg gtctggccca gctggcttcc    3060
ccagcccctc agccatccag ggctacccac tgcttactca gggaccaggc agcccccatg    3120
gcagtaaaag cagcctagac agaacctgca gctctgtgga agaggcaaa gtcctgaaaa    3180 ggcaaagggt tgtcacttag ggcagcttct ccaactttaa catgcatcca agtcacctgg    3240
gaatgttgtt aaaatcagga gatctggggt ggggcctagg actctgcatt tcttacagat    3300
tcccaggtga gctgatgctg gtggttaagg gtagcaaatc tctaaagcac gaagccctca    3360
caaatctttg ccatttccca aacactccgc tccatggtct ccagtcatca gagcaactct    3420
acctggtatt atcatcccca ttttacagat aatgacactg aggctcagaa aggttgagga    3480
taagcccact ttcctgtcat tagtggcagc cccagatcca gacctaggcc tcctggcacc    3540
cagtccactg gcagtggaat tgctttcctg agaatcattc tgaggctggg ctattgcttc    3600
tcccttgctt caaagaatct agcagcgggg gataggattt gcaacaaaa agctgaccca    3660 gaggccatac agagcaggaa tatcccattg cccctcctc cactgggttc agagggtaag    3720
aaagcaccct ccaataaacc caggctccag gccgtggggg ctgctgaagg ctctttcccc    3780
gcaagggcca ggtgttgaca ccttaaagct ggcgcccca gccccactct tggctgtgct    3840
ggccaggtga ctcctagttc ttggccacat catcagaaag tcaaaggtct cactccaggt    3900
ttggggctcc ttccttccac tcccctccct gccagagtct gtcttggcca gtgccagcct    3960
cgatgctttg gttttgaccc cacctgatcc tcctttcctc atgcagcaca agtgctcacc    4020
ggggccagag ccagggcatg gatatgacaa gcagggcagc ctggacactg ccctcacagg    4080
acagcgccaa taacaataca gtgtctgagt atctccaggg gatgatttct ggctctttgt    4140
ctccaatcag tcccactccc tcctgaggtc cccaagggca gtattcagag aggtttcctg    4200
cgttttattt ctatttggta taccctccac tgttgtccac tgccctgtgt ggccttctgg    4260
ttgacctctg cccgatcttc tgtctctctg agggaatcag agtccagcat ccagccccag    4320
ctggaacagc tgaagtcaca agcctcctct aagccaaggc cagtgtgttc agaggtgact    4380
gccacccata ctaggacaaa cacagctcag atcaccaggt caagcaccta ggcctggctt    4440
ctcctgagac agaggactca gaagtggcct ttcctccaaa gcctgctcag acacaggtct    4500
gtagggccag ggtgttctgc ttggctgggc tgcagctgct acccctcggt tggggctgag    4560
tcagccagat cctcccccta cttctcccca agggccaaga actgctcagg gacattaaag    4620
gtcaaaagtc cagccacact cattcatcct ttccccaggc ccatgaagag aggcatctca    4680
ttgtagaatg tatgaggaag tgggaagtat ctcagagaat cagctaagtt tcctaacttg    4740
tccatccaaa tgtgatcacc acgattcaac aatttggggc attgctgatc tagccgttcc    4800
tagtggggct tgctcaaggt tgcacagcga gtcagtagaa gccctggctg gccccacttg    4860
gtaccaatcc accaggcagc tcagggctcc tgcccagccc agcagcttct gttgtctaac    4920
gtatggcagg cagactggga gcaggaaaac agagggcccc aaagcccaag gcaccagaag    4980
gtttgtttca gtttgctgaa gctgatttgt aatgattggc actcttcagc caggggagtg    5040
ggtaggccat agccaaggat cgattcccca accacagcaa aggcaacact cttcctccag    5100
agatcaccaa gccctcttaa cctccctccc tccttcccaa ggctggcact aaccaggtac    5160
cacattcatt gttaaggaat ggctgatgac tgctacacgt gttgggaacc tggttgggc    5220 tgtgcagttt gggctggaag gagagatgcc agccctcgtg ctgcctctgg tccctgaagt    5280
gtcacctctc tcaggacctc tcctctgccc tgtggggtta taagtgatgg atagcagaaa    5340
gggagaactg actcctgtcc caaatagctc ctctgccacc tgtcctgcag tgggcctgtg    5400
```

```
tgggttatga ttctagatcc tagacagagg ctgggtcagc tgtggatggg gtggtgcctt    5460
ggtctctctt gactacctcg tccaaagaga gcactgccct tagacaagag ttgcttgtcc    5520
tgctgtgggc tgggcttcca gctgcagacc tccagttgct tggtgttcac tttgctcctc    5580
ttgccctctg tcttctggtc caggcagatc aggggctctg gggaaactgc tggaactcga    5640
ggtgaggatc agccttttcc agcatcctgt gagagaccag agagagagtt tggatttcat    5700
gtggggaacc ctcaaggcct gtctggagaa gtgacacagg atttactggg gtgggctggt    5760
ccaggtagct ctcctgaacc tcctccttcc ccaagctgag aagctgagag ctggaggaca    5820
atatccaggg acatggctct ggaaaataac tttttttttt ttaagagaca gggtcttgct    5880
ctgttgtcca ggctggaggg cagtgacata atcatagctc actgtaccct tgaactcctg    5940
ggctcaagtg atcctcctgc ctcagcctcc ttagtagctg gactaccag tgcataccac    6000 catgcctggg tgatttttta aattttttat acagacaagg tcttgctatg ttgcccaggc    6060
tgatcttgaa ttcccgggct caagtggtcc tcctgcctca gcctcccaca ggatcgggat    6120
tacaggcaag agcctccacg cccggccatg aaatataatt cttaatatca tacaggaaaa    6180
agtcagcggg tcaagctagc ctgtggccca gccacaacta gctgacaaag cttcctggcc    6240 ttcccttta cacagttctg ctgccatagt tccatctata aaatgggaat ggagggaaat    6300
aggggaactg gatagagaa cacagccttg ccaagcagca atgttagcct gatccttcct    6360
ccacctagct cgccatctcg cccttggaaa atggctcctg gaggattagg cagccatctg    6420
caaggagagg ggcaacctgg gacaagacac ccagagggta aggattccag gaatgaagct    6480
gccatttctg gttgggagga aagaggaaa cttttaagag aaagggctcc attatgagca    6540
tgggttcagg gccctgcatt acccaatcag aacagccggg atgagcagga ggccagctcc    6600
caggaggaag gggaacccct tcataaagtt cagagtggct gggtagagtg agttgaagat    6660
gccggaggcc gtcagcatgg ccaggctatt cacacaggcc acagcagaaa agagagcacc    6720
tgtgaagaaa taaataccat actctggagt ccgaagggc catattccaa ctctggcacc    6780
accacctcac agctgtgtga ccgggagtag tcacttaacc tatgtctccc cttcctcacc    6840
agtaaatcct gctacatcat gtactgtgac aaggattcag taaggtcata tgtgacagt    6900 agctggcaca gagggctac taaacaaatg gctgctatta aatccacatt aaaagtacat    6960
gtgatctgac agaacccagc acataaaaga aaaaaaaag t                       7001
```

<210> SEQ ID NO 2
<211> LENGTH: 724
<212> TYPE: PRT
<213> ORGANISM: Homo sapiens
<300> PUBLICATION INFORMATION:
<308> DATABASE ACCESSION NUMBER: GenBank Accession No. NP_055892

<400> SEQUENCE: 2

```
Met Val Leu Thr Leu Leu Leu Ser Ala Tyr Lys Leu Cys Arg Phe Phe
 1               5                  10                  15

Ala Met Ser Gly Pro Arg Pro Gly Ala Glu Arg Leu Ala Val Pro Gly
                20                  25                  30

Pro Asp Gly Gly Gly Thr Gly Pro Trp Trp Ala Ala Gly Gly Arg
            35                  40                  45

Gly Pro Arg Glu Val Ser Pro Gly Ala Gly Thr Glu Val Gln Asp Ala
        50                  55                  60

Leu Glu Arg Ala Leu Pro Glu Leu Gln Gln Ala Leu Ser Ala Leu Lys
65                  70                  75                  80
```

-continued

Gln Ala Gly Gly Ala Arg Ala Val Gly Ala Gly Leu Ala Glu Val Phe
                        85                  90                  95

Gln Leu Val Glu Glu Ala Trp Leu Leu Pro Ala Val Gly Arg Glu Val
                    100                 105                 110

Ala Gln Gly Leu Cys Asp Ala Ile Arg Leu Asp Gly Gly Leu Asp Leu
                115                 120                 125

Leu Leu Arg Leu Leu Gln Ala Pro Glu Leu Glu Thr Arg Val Gln Ala
            130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                        165                 170                 175

Pro Val Glu Leu Ala Arg Ser Val Ala Gly Ile Leu Glu His Met Phe
                    180                 185                 190

Lys His Ser Glu Glu Thr Cys Gln Arg Leu Val Ala Ala Gly Gly Leu
                195                 200                 205

Asp Ala Val Leu Tyr Trp Cys Arg Arg Thr Asp Pro Ala Leu Leu Arg
            210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                        245                 250                 255

Leu Ala Phe Ser Lys Glu Asp Glu Leu Leu Arg Leu His Ala Cys Leu
                    260                 265                 270

Ala Val Ala Val Leu Ala Thr Asn Lys Glu Val Glu Arg Glu Val Glu
                275                 280                 285

Arg Ser Gly Thr Leu Ala Leu Val Glu Pro Leu Val Ala Ser Leu Asp
            290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                        325                 330                 335

Asn Arg Leu Glu Ala Gln Cys Ile Gly Ala Phe Tyr Leu Cys Ala Glu
                    340                 345                 350

Ala Ala Ile Lys Ser Leu Gln Gly Lys Thr Lys Val Phe Ser Asp Ile
                355                 360                 365

Gly Ala Ile Gln Ser Leu Lys Arg Leu Val Ser Tyr Ser Thr Asn Gly
            370                 375                 380

Thr Lys Ser Ala Leu Ala Lys Arg Ala Leu Arg Leu Leu Gly Glu Glu
385                 390                 395                 400

Val Pro Arg Pro Ile Leu Pro Ser Val Pro Ser Trp Lys Glu Ala Glu
                        405                 410                 415

Val Gln Thr Trp Leu Gln Gln Ile Gly Phe Ser Lys Tyr Cys Glu Ser
                    420                 425                 430

Phe Arg Glu Gln Gln Val Asp Gly Asp Leu Leu Leu Arg Leu Thr Glu
                435                 440                 445

Glu Glu Leu Gln Thr Asp Leu Gly Met Lys Ser Gly Ile Thr Arg Lys
            450                 455                 460

Arg Phe Phe Arg Glu Leu Thr Glu Leu Lys Thr Phe Ala Asn Tyr Ser
465                 470                 475                 480

Thr Cys Asp Arg Ser Asn Leu Ala Asp Trp Leu Gly Ser Leu Asp Pro
                        485                 490                 495

```
Arg Phe Arg Gln Tyr Thr Tyr Gly Leu Val Ser Cys Gly Leu Asp Arg
            500                 505                 510
Ser Leu Leu His Arg Val Ser Glu Gln Gln Leu Leu Glu Asp Cys Gly
        515                 520                 525
Ile His Leu Gly Val His Arg Ala Arg Ile Leu Thr Ala Ala Arg Glu
    530                 535                 540
Met Leu His Ser Pro Leu Pro Cys Thr Gly Gly Lys Pro Ser Gly Asp
545                 550                 555                 560
Thr Pro Asp Val Phe Ile Ser Tyr Arg Arg Asn Ser Gly Ser Gln Leu
                565                 570                 575
Ala Ser Leu Leu Lys Val His Leu Gln Leu His Gly Phe Ser Val Phe
            580                 585                 590
Ile Asp Val Glu Lys Leu Glu Ala Gly Lys Phe Glu Asp Lys Leu Ile
        595                 600                 605
Gln Ser Val Met Gly Ala Arg Asn Phe Val Leu Val Leu Ser Pro Gly
    610                 615                 620
Ala Leu Asp Lys Cys Met Gln Asp His Asp Cys Lys Asp Trp Val His
625                 630                 635                 640
Lys Glu Ile Val Thr Ala Leu Ser Cys Gly Lys Asn Ile Val Pro Ile
                645                 650                 655
Ile Asp Gly Phe Glu Trp Pro Glu Pro Gln Val Leu Pro Glu Asp Met
            660                 665                 670
Gln Ala Val Leu Thr Phe Asn Gly Ile Lys Trp Ser His Glu Tyr Gln
        675                 680                 685
Glu Ala Thr Ile Glu Lys Ile Ile Arg Phe Leu Gln Gly Arg Ser Ser
    690                 695                 700
Arg Asp Ser Ser Ala Gly Ser Asp Thr Ser Leu Glu Gly Ala Ala Pro
705                 710                 715                 720
Met Gly Pro Thr

<210> SEQ ID NO 3
<211> LENGTH: 5164
<212> TYPE: DNA
<213> ORGANISM: Mus musculus
<300> PUBLICATION INFORMATION:
<308> DATABASE ACCESSION NUMBER: GenBank Accession No. NM_001168521

<400> SEQUENCE: 3
ctgttgagca tcttagctcc gctgtgctta gattggagca gcgctttgtt ccgggcaccg    60
gcgtctctac cctcccgcgt ctggtccatg cttctctctc ccttcatgcc cttcctaagt   120
cgctgagtcc cggagctgcc ctcctccttc tgcttctaca cttgtagccc agcaccttta   180
ccggatcctg tttgcttttt ttttttttt ttttttcctt tctcctccca aggccggggt    240
ctctctgcca ggccccgccc ctctaggcct ggcatgtccc ctgctgccca gcgcccatgg   300
tcctgacgct gctcttctcc gcctacaaac tgtgccgctt cttcaccatg tcaggcccac   360
ggccgggcgc cgatcggctg acagtgcccg gaccggatcg gagtggtggc gccagcccat   420
ggtgggctgc gggcggtcgc gggtctcgcg aagtgtcgcc cggagtgggc actgaggtgc   480
aaggcgccct ggagcgttcg ctgcctgagc tgcagcaggc gctgtccgag ctgaaacagg   540
caagcgcggc gcgggctgtg ggcgcgggtc tcgccgaggt cttccagctg gtagaggaag   600
cctggctgct gccggccgtg ggccgcgagg tgcccaaggg tctatgcgat gctatacgtc   660
tggacggtgg cctcgacttg ctgttgcggc tgcttcaggc accggagcta gagacccgtg   720
tgcaggccgc gcgcttgctg gagcagatcc tggtggctga gaaccgggac gcgtggcgc    780
```

-continued

| | |
|---|---|
| gcatcggtct aggcgtgatc ttgaacctgg cgaaggagcg cgagcctgtg aactggcac | 840 |
| gaagcgtggc gggcatcttg gagcacatgt tcaagcactc ggaggagacg tgccagcggc | 900 |
| tggtggcggc cggaggcctc gacgcggtgc tgtactggtg ccgccgcaca gacccggcgc | 960 |
| tgctgcgcca ctgcgctctt gcgctggcga actgcgcgct gcacggggc cagacggtgc | 1020 |
| agcggtgcat ggtggagaag cgcgccgccg agtggctctt cccgctcgct ttctccaagg | 1080 |
| aggacgagct gctgcggctg cacgcctgcc tggcggtggc ggtgttggct accaacaagg | 1140 |
| aggtggaacg cgaggtcgag cattctggca cattggcgct tgtcgagccg ctcgtggcat | 1200 |
| cgctggaccc cggccgcttc gcccgctgcc tggtggatgc cagtgacaca gccagggtc | 1260 |
| gtggaccaga cgacctgcag agcctggtgc tgttgctcga ttcgtcgcgt ttggaggctc | 1320 |
| agtgcatagg agcattctac ctgtgcgcag aggctgccat caagagccta cagggaaaga | 1380 |
| ccaaggtgtt cagcgacatc ggcgctatcc agagcctgaa cgcctggtt tcttactcta | 1440 |
| cgaatggcac cacgtcggcg ctggccaagc gcgcgctgcg cctattgggc gaggaggtgc | 1500 |
| caaggcgcat cctgccctgc gtggccagct ggaaggaagc tgaggtccag acctggctac | 1560 |
| agcagatcgg cttctcccag tactgcgaga actttcggga gcagcaggta gatggtgacc | 1620 |
| tgcttctaag actcacagat gaagaactcc agacagacct aggcatgaaa tcaagcatca | 1680 |
| cccgcaagag gttctttagg gagctcacag agctcaagac cttcgccagc tacgctactt | 1740 |
| gcgaccgcag caacctagcg gactggctgg gcagcctgga tcctcgcttc cgccagtaca | 1800 |
| cctatgccct ggtcagctgc ggtctggacc gctccctgct gcaccgcgtg tcagagcagc | 1860 |
| agctcctgga ggactgtggc atccgcctgg gagtgcaccg cacgcgcatc ctctctgcag | 1920 |
| ccagaggtca ctttgcccag actgcctga gaagcttgag gagaccaagt ctccacgatg | 1980 |
| atggaccccg tgataagcag tggggaagag ccaccctcac ctccatgtct ctttccttgg | 2040 |
| ctccagaaat gctacattcc ccgctgccct gtactggagg caagctcagt ggggacaccc | 2100 |
| cagatgtctt tatcagttac cggaggaact cagggtccca gctggccagc tcctgaagg | 2160 |
| tgcacctgca gcttcacggc ttcagcgtct tcatcgacgt ggagaagctg aagccggca | 2220 |
| aattcgagga caagcttatc caaagcgtca tagcggctcg caattttgtc ctggtgctgt | 2280 |
| ctgctgggc gctggataag tgcatgcagg accatgactg caaggactgg gtgcacaagg | 2340 |
| agattgtgac tgctttaagc tgtggcaaga acattgtgcc catcattgat ggctttgagt | 2400 |
| ggcctgagcc tcaggcgctg cctgaggata tgcaggctgt actcaccttc aacggcatca | 2460 |
| aatggtccca tgagtaccag gaggccacca tcgagaagat catccgcttc ctacagggcc | 2520 |
| gcccctctca ggactcctct gccggatcgg ataccagttt ggagggagct acgccaatgg | 2580 |
| gtctgcctta acctgtcccc agttcccgtg ccctactgtg actcctgatt tagttccctg | 2640 |
| cccttaaagg aatagctcct ctagatgcca ccctgactga ggcaaaccag actgttctca | 2700 |
| ggcaatggct ttcccggctg ccactctgtg gcccacttct aatccagaga tgccaggcac | 2760 |
| aggttagatg agaggacact cctgtgtcag gccctgccat caggacccag ctcccatgca | 2820 |
| gaaccatgtc cctgcttagt tctggacatc caagacaggg gaagaacatt tccccatctc | 2880 |
| ctgacctgag agcagccagc ttgagtaagg tgaggttgcc agcctccat aagggtcaat | 2940 |
| acaacgcctg gatccccaaa cctgtgctca ggaggaagct ggggctgaga atccccaag | 3000 |
| gctatctact cacattgtgc ctggaccgg gctcacctgg cttcctcctg cctcatggcc | 3060 |
| ttgctctgta actacctggt accccttcta gacttccttt aggcagcctc ctttggcata | 3120 |

| | | | | |
|---|---|---|---|---|
| ttgggagtca | gggtgtggct | gaactggacc | tctgcctggc | cttgttgctc | ctcctggtgc | 3180 |
| aagaagggt | gctttgctta | tgcaaggaga | ccataagagc | tcactctagc | ccaaacctttt | 3240 |
| gtgcgtgcct | aaggctctta | cctagcctgc | tccatctgac | ttccccagct | cctcacccac | 3300 |
| acagagcttg | tcacccacct | gctcagggaa | gccccaacac | caccagtagc | ccgagcagaa | 3360 |
| cctgcaccat | gggaaaaagg | caagccatcc | acaggcaagg | gctaattcct | ggggcagttt | 3420 |
| ctcccaccga | agtgtgtcaa | atccattggg | aatctcatca | aaattcagag | caggccacct | 3480 |
| gggaagcacc | tgggcctctg | catttttcag | attcccagga | gagctgatga | aagagagccc | 3540 |
| tcactaatcc | agccattcca | aacaccccca | ccctggtccc | tgatcatcac | aacagccttt | 3600 |
| tcctctctcc | agttttacag | agctgagtgg | ctgagtgatg | ggatcaggtc | cccaagttat | 3660 |
| tggtggcagc | ctcaggatct | tgccttagtc | ctggtaccca | gatctgttct | cctgagactc | 3720 |
| atccaagagg | ctgtggccca | tgcttggtag | ctgcctctcc | ctggccacaa | agaactgagc | 3780 |
| agtgcagggt | gggtcttgac | taaaaggtgg | agctaagggc | atatagaatg | tcccatgtcc | 3840 |
| ctccctccac | tggacaagaa | aggcaagaaa | gctggctctt | gccattaccc | aggctcaagc | 3900 |
| tcagagagct | ggcaccaccc | tgctgtcgtc | ttctggaggc | catggggtca | cacctctcct | 3960 |
| gaggctagcc | aggttacttg | cccacggccc | acattatcag | agagccaaag | ggcttttctct | 4020 |
| ccaggcctgg | ggacactttc | ctcctaccgt | ccatcttcca | tgggtcatgg | ctggcctctg | 4080 |
| gctgtgacta | tttgcagttt | tgtcaccagg | aacaacccc | gcatcctatt | ctgaggtgag | 4140 |
| gcagatggaa | tggtatcctt | gatgacaaat | tcaatgacaa | tacagtgtat | gagttcaccc | 4200 |
| taaggaaatg | tctgtcttca | gtcccatact | ctccagtggt | ccctgtgggc | agtacttaag | 4260 |
| aaatttctgg | ttttccttgt | tgggggcaca | agtcactact | acctccactg | tctggccttc | 4320 |
| tgttgatctg | tcccctactg | tcttcttggg | gaaccagagc | acagcctttat | gtcccagcca | 4380 |
| ggatagcaaa | agtgtcaagc | ctcctctagc | tagacagtac | actgtgtggt | gacagagggc | 4440 |
| ctcaacttct | gctaagcatg | gctgaccaca | ctgatcttga | acaggctct | tcagtagccc | 4500 |
| ttcaagcagc | ccacactcgc | atggtctgtg | ggttcagggt | ttcttcctag | ctgagctata | 4560 |
| gctgctgccc | ccagattggg | gcctagtcag | ggagatccct | actcttcaac | acccaccgtc | 4620 |
| tctagggagc | tacgaactgc | ttaggaacat | taagaggcta | aagatccagc | cagtttgttc | 4680 |
| atccttcact | gagcatctca | tcctgggatg | tatggagctg | gagggatctc | agagcatcca | 4740 |
| acagctgtgc | ttcctaacgc | atccagttag | gtccttgcag | acagatgtgg | gggagtgctg | 4800 |
| atccagtttt | ctctagattt | gctcaaggtc | acatgctgcc | agagtgaagc | ctttccctcc | 4860 |
| tcacagcctc | agggcagtgg | ggttagtgga | aagcctcttc | ttgcttagac | ttttctattt | 4920 |
| ccagagggac | agtgaagcag | aagtgtggaa | gccagatggg | ccctggtgca | gttcagtggg | 4980 |
| ccttagtttt | ccctgggatg | tatctctttc | acctgcatgg | tttccagctg | ggaaactagc | 5040 |
| ttgcagtttg | ggcaggaaga | gatagcttca | tcaaagacag | tggcttccca | ttagataaga | 5100 |
| ttctaccttt | cagttttgag | cccaggtctt | tccaacacgc | cacacataca | cacacacaca | 5160 |
| caca | | | | | 5164 |

<210> SEQ ID NO 4
<211> LENGTH: 764
<212> TYPE: PRT
<213> ORGANISM: Mus musculus
<300> PUBLICATION INFORMATION:
<308> DATABASE ACCESSION NUMBER: GenBank Accession No. NP_001161993

<400> SEQUENCE: 4

```
Met Val Leu Thr Leu Leu Phe Ser Ala Tyr Lys Leu Cys Arg Phe Phe
 1               5                  10                  15

Thr Met Ser Gly Pro Arg Pro Gly Ala Asp Arg Leu Thr Val Pro Gly
             20                  25                  30

Pro Asp Arg Ser Gly Gly Ala Ser Pro Trp Trp Ala Ala Gly Gly Arg
         35                  40                  45

Gly Ser Arg Glu Val Ser Pro Gly Val Gly Thr Glu Val Gln Gly Ala
     50                  55                  60

Leu Glu Arg Ser Leu Pro Glu Leu Gln Gln Ala Leu Ser Glu Leu Lys
 65                  70                  75                  80

Gln Ala Ser Ala Ala Arg Ala Val Gly Ala Gly Leu Ala Glu Val Phe
                 85                  90                  95

Gln Leu Val Glu Glu Ala Trp Leu Leu Pro Ala Val Gly Arg Glu Val
             100                 105                 110

Ala Gln Gly Leu Cys Asp Ala Ile Arg Leu Asp Gly Gly Leu Asp Leu
         115                 120                 125

Leu Leu Arg Leu Leu Gln Ala Pro Glu Leu Glu Thr Arg Val Gln Ala
130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Lys His Ser Glu Glu Thr Cys Gln Arg Leu Val Ala Ala Gly Gly Leu
        195                 200                 205

Asp Ala Val Leu Tyr Trp Cys Arg Arg Thr Asp Pro Ala Leu Leu Arg
    210                 215                 220

His Cys Ala Leu Ala Leu Ala Asn Cys Ala Leu His Gly Gly Gln Thr
225                 230                 235                 240

Val Gln Arg Cys Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270

Ala Val Ala Val Leu Ala Thr Asn Lys Glu Val Glu Arg Glu Val Glu
        275                 280                 285

His Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Ser Leu Val Leu Leu Asp Ser
                325                 330                 335

Ser Arg Leu Glu Ala Gln Cys Ile Gly Ala Phe Tyr Leu Cys Ala Glu
            340                 345                 350

Ala Ala Ile Lys Ser Leu Gln Gly Lys Thr Lys Val Phe Ser Asp Ile
        355                 360                 365

Gly Ala Ile Gln Ser Leu Lys Arg Leu Val Ser Tyr Ser Thr Asn Gly
    370                 375                 380

Thr Thr Ser Ala Leu Ala Lys Arg Ala Leu Arg Leu Leu Gly Glu Glu
385                 390                 395                 400

Val Pro Arg Arg Ile Leu Pro Cys Val Ala Ser Trp Lys Glu Ala Glu
                405                 410                 415
```

Val Gln Thr Trp Leu Gln Gln Ile Gly Phe Ser Gln Tyr Cys Glu Asn
            420                 425                 430

Phe Arg Glu Gln Gln Val Asp Gly Asp Leu Leu Arg Leu Thr Asp
        435                 440                 445

Glu Glu Leu Gln Thr Asp Leu Gly Met Lys Ser Ser Ile Thr Arg Lys
    450                 455                 460

Arg Phe Phe Arg Glu Leu Thr Glu Leu Lys Thr Phe Ala Ser Tyr Ala
465                 470                 475                 480

Thr Cys Asp Arg Ser Asn Leu Ala Asp Trp Leu Gly Ser Leu Asp Pro
                485                 490                 495

Arg Phe Arg Gln Tyr Thr Tyr Gly Leu Val Ser Cys Gly Leu Asp Arg
            500                 505                 510

Ser Leu Leu His Arg Val Ser Glu Gln Leu Leu Glu Asp Cys Gly
        515                 520                 525

Ile Arg Leu Gly Val His Arg Thr Arg Ile Leu Ser Ala Ala Arg Gly
    530                 535                 540

His Phe Ala Gln Thr Gly Leu Arg Ser Leu Arg Arg Pro Ser Leu His
545                 550                 555                 560

Asp Asp Gly Pro Arg Asp Lys Gln Trp Gly Arg Ala Thr Leu Thr Ser
                565                 570                 575

Met Ser Leu Ser Leu Ala Pro Glu Met Leu His Ser Pro Leu Pro Cys
            580                 585                 590

Thr Gly Gly Lys Leu Ser Gly Asp Thr Pro Asp Val Phe Ile Ser Tyr
        595                 600                 605

Arg Arg Asn Ser Gly Ser Gln Leu Ala Ser Leu Leu Lys Val His Leu
610                 615                 620

Gln Leu His Gly Phe Ser Val Phe Ile Asp Val Glu Lys Leu Glu Ala
625                 630                 635                 640

Gly Lys Phe Glu Asp Lys Leu Ile Gln Ser Val Ile Ala Ala Arg Asn
                645                 650                 655

Phe Val Leu Val Leu Ser Ala Gly Ala Leu Asp Lys Cys Met Gln Asp
            660                 665                 670

His Asp Cys Lys Asp Trp Val His Lys Glu Ile Val Thr Ala Leu Ser
        675                 680                 685

Cys Gly Lys Asn Ile Val Pro Ile Ile Asp Gly Phe Glu Trp Pro Glu
    690                 695                 700

Pro Gln Ala Leu Pro Glu Asp Met Gln Ala Val Leu Thr Phe Asn Gly
705                 710                 715                 720

Ile Lys Trp Ser His Glu Tyr Gln Glu Ala Thr Ile Glu Lys Ile Ile
                725                 730                 735

Arg Phe Leu Gln Gly Arg Pro Ser Gln Asp Ser Ser Ala Gly Ser Asp
            740                 745                 750

Thr Ser Leu Glu Gly Ala Thr Pro Met Gly Leu Pro
        755                 760

<210> SEQ ID NO 5
<211> LENGTH: 5044
<212> TYPE: DNA
<213> ORGANISM: Mus musculus
<300> PUBLICATION INFORMATION:
<308> DATABASE ACCESSION NUMBER: GenBank Accession No. NM_172795

<400> SEQUENCE: 5
ctgttgagca tcttagctcc gctgtgctta gattggagca gcgctttgtt ccgggcaccg      60
gcgtctctac cctcccgcgt ctggtccatg cttctctctc ccttcatgcc cttcctaagt     120

```
cgctgagtcc cggagctgcc ctcctccttc tgcttctaca cttgtagccc agcaccttta    180
ccggatcctg tttgctttttt tttttttttt ttttttttctt tctcctccca aggccggggt   240
ctctctgcca ggccccgccc ctctaggcct ggcatgtccc ctgctgccca gcgcccatgg    300
tcctgacgct gctcttctcc gcctacaaac tgtgccgctt cttcaccatg tcaggcccac    360
ggccgggcgc cgatcggctg acagtgcccg gaccggatcg gagtggtggc gccagcccat    420
ggtgggctgc gggcggtcgc gggtctcgcg aagtgtcgcc cggagtgggc actgaggtgc    480
aaggcgccct ggagcgttcg ctgcctgagc tgcagcaggc gctgtccgag ctgaaacagg    540
caagcgcggc gcgggctgtg ggcgcgggtc tcgccgaggt cttccagctg gtagaggaag    600
cctggctgct gccggccgtg ggccgcgagg tggcccaagg tctatgcgat gctatacgtc    660
tggacggtgg cctcgacttg ctgttgcggc tgcttcaggc accggagcta gagacccgtg    720
tgcaggccgc gcgcttgctg agcagatcc tggtggctga aaccgggac cgcgtggcgc    780 gcatcggtct aggcgtgatc ttgaacctgg cgaaggagcg cgagcctgtg gaactggcac    840
gaagcgtggc gggcatcttg gagcacatgt tcaagcactc ggaggagacg tgccagcggc    900
tggtggcggc cggaggcctc gacgcggtgc tgtactggtg ccgccgcaca gacccggcgc    960
tgctgcgcca ctgcgctctt gcgctggcga actgcgcgct gcacggggc cagacggtgc    1020 agcggtgcat ggtggagaag cgcgccgccg agtggctctt cccgctcgct ttctccaagg    1080
aggacgagct gctgcggctg cacgcctgcc tggcggtggc ggtgttggct accaacaagg    1140
aggtggaacg cgaggtcgag cattctggca cattggcgct tgtcgagccg ctcgtggcat    1200
cgctggaccc cggccgcttc gcccgctgcc tggtggatgc cagtgacaca agccagggtc    1260
gtggaccaga cgacctgcag agcctggtgc tgttgctcga ttcgtcgcgt ttggaggctc    1320
agtgcatagg agcattctac ctgtgcgcag aggctgccat caagagccta cagggaaaga    1380
ccaaggtgtt cagcgacatc ggcgctatcc agagcctgaa acgccgtggtt tcttactcta   1440 cgaatggcac cacgtcggcg ctggccaagc gcgcgctgcg cctattgggc gaggaggtgc    1500
caaggcgcat cctgccctgc gtggccagct ggaaggaagc tgaggtccag acctggctac    1560
agcagatcgg cttctcccag tactgcgaga actttcggga gcagcaggta gatggtgacc    1620
tgcttctaag actcacagat gaagaactcc agacagacct aggcatgaaa tcaagcatca    1680
cccgcaagag gttctttagg gagctcacag agctcaagac cttcgccagc tacgctactt    1740
gcgaccgcag caacctagcg gactggctgg gcagcctgga tcctcgcttc gccagtaca    1800 cctatgcct ggtcagctgc ggtctggacc gctcccctgct gcaccgcgtg tcagagcagc    1860
agctcctgga ggactgtggc atccgcctgg gagtgcaccg cacgcgcatc ctctctgcag    1920
ccagagaaat gctacattcc ccgctgccct gtactggagg caagctcagt ggggacaccc    1980
cagatgtctt tatcagttac cggaggaact cagggtccca gctggccagc ctcctgaagg    2040
tgcacctgca gcttcacggc ttcagcgtct tcatcgacgt ggagaagctg aagccggca    2100 aattcgagga caagcttatc caaagcgtca tagcggctcg caattttgtc ctggtgctgt    2160 ctgctgggc gctggataag tgcatgcagg accatgactg caaggactgg gtgcacaagg    2220
agattgtgac tgctttaagc tgtggcaaga acattgtgcc catcattgat ggctttgagt    2280
ggcctgagcc tcaggcgctg cctgaggata tgcaggctgt actcaccttc aacggcatca    2340
aatggtccca tgagtaccag gaggccacca tcgagaagat catccgcttc ctacagggcc    2400
gcccctctca ggactcctct gccggatcgg ataccagttt ggagggagct acgccaatgg    2460
```

```
gtctgcctta acctgtcccc agttcccgtg ccctactgtg actcctgatt tagttccctg    2520
cccttaaagg aatagctcct ctagatgcca ccctgactga ggcaaaccag actgttctca    2580
ggcaatggct ttcccggctg ccactctgtg gcccacttct aatccagaga tgccaggcac    2640
aggttagatg agaggacact cctgtgtcag gccctgccat caggacccag ctcccatgca    2700
gaaccatgtc cctgcttagt tctggacatc aagacaggg gaagaacatt tccccatctc    2760
ctgacctgag agcagccagc ttgagtaagg tgaggttgcc agcctcccat aagggtcaat    2820
acaacgcctg gatccccaaa cctgtgctca ggaggaagct ggggctgaga atcccccaag    2880
gctatctact cacattgtgc ctggacccgg gctcacctgg cttcctcctg cctcatggcc    2940
ttgctctgta actacctggt accccttcta gacttccttt aggcagcctc ctttggcata    3000 ttggagtca gggtgtggct gaactggacc tctgcctggc cttgttgctc ctcctggtgc    3060 aagaagggt gctttgctta tgcaaggaga ccataagagc tcactctagc ccaaaccttt    3120
gtgcgtgcct aaggctctta cctagcctgc tccatctgac ttccccagct cctcacccac    3180
acagagcttg tcacccacct gctcaggaa gccccaacac caccagtagc ccgagcagaa    3240
cctgcaccat gggaaaaagg caagccatcc acaggcaagg gctaattcct ggggcagttt    3300
ctcccaccga agtgtgtcaa atccattggg aatctcatca aaattcagag caggccacct    3360
gggaagcacc tgggcctctg cattttcag attcccagga gagctgatga aagagagccc    3420
tcactaatcc agccattcca aacaccccca ccctggtccc tgatcatcac aacagccttt    3480
tcctctctcc agttttacag agctgagtgg ctgagtgatg ggatcaggtc cccaagttat    3540
tggtggcagc ctcaggatct tgccttagtc ctggtaccca gatctgttct cctgagactc    3600
atccaagagg ctgtggccca tgcttggtag ctgcctctcc ctggccacaa agaactgagc    3660
agtgcagggt gggtcttgac taaaaggtgg agctaagggc atatagaatg tcccatgtcc    3720
ctccctccac tggacaagaa aggcaagaaa gctggctctt gccattaccc aggctcaagc    3780
tcagagagct ggcaccaccc tgctgtcgtc ttctggaggc catggggtca cacctctcct    3840
gaggctagcc aggttacttg cccacggccc acattatcag agagccaaag ggctttctct    3900
ccaggcctgg ggacactttc ctcctaccgt ccatcttcca tgggtcatgg ctggcctctg    3960
gctgtgacta tttgcagttt tgtcaccagg aacaaccccc gcatcctatt ctgaggtgag    4020
gcagatggaa tggtatcctt gatgacaaat tcaatgacaa tacagtgtat gagttcaccc    4080
taaggaaatg tctgtcttca gtcccatact ctccagtggt ccctgtgggc agtacttaag    4140
aaatttctgg ttttccttgt ttggggcaca agtcactact acctccactg tctggccttc    4200
tgttgatctg tcccctactg tcttcttggg gaaccagagc acagccttat gtcccagcca    4260
ggatagcaaa agtgtcaagc ctcctctagc tagacagtac actgtgtggt gacagagggc    4320
ctcaacttct gctaagcatg gctgaccaca ctgatcttga gacaggctct tcagtagccc    4380
ttcaagcagc ccacactcgc atggtctgtg ggttcagggt ttcttcctag ctgagctata    4440
gctgctgccc ccagattggg gcctagtcag ggagatccct actcttcaac acccaccgtc    4500
tctagggagc tacgaactgc ttaggaacat taagaggcta agatccagc cagtttgttc     4560 atccttcact gagcatctca tcctgggatg tatggagctg gagggatctc agagcatcca    4620
acagctgtgc ttcctaacgc atccagttag gtccttgcag acagatgtgg gggagtgctg    4680
atccagtttt ctctagattt gctcaaggtc acatgctgcc agagtgaagc ctttccctcc    4740
tcacagcctc agggcagtgg ggttagtgga aagcctcttc ttgcttagac ttttctattt    4800
ccagagggac agtgaagcag aagtgtggaa gccagatggg ccctggtgca gttcagtggg    4860
```

```
cttagttttt ccctgggatg tatctctttc acctgcatgg tttccagctg ggaaactagc    4920
ttgcagtttg ggcaggaaga gatagcttca tcaaagacag tggcttccca ttagataaga    4980
ttctaccttt cagttttgag cccaggtctt tccaacacgc cacacataca cacacacaca   5040
caca                                                                 5044

<210> SEQ ID NO 6
<211> LENGTH: 724
<212> TYPE: PRT
<213> ORGANISM: Mus musculus
<300> PUBLICATION INFORMATION:
<308> DATABASE ACCESSION NUMBER: GenBank Accession No. NP_766383

<400> SEQUENCE: 6

Met Val Leu Thr Leu Leu Phe Ser Ala Tyr Lys Leu Cys Arg Phe Phe
  1               5                  10                  15

Thr Met Ser Gly Pro Arg Pro Gly Ala Asp Arg Leu Thr Val Pro Gly
                 20                  25                  30

Pro Asp Arg Ser Gly Gly Ala Ser Pro Trp Trp Ala Ala Gly Gly Arg
             35                  40                  45

Gly Ser Arg Glu Val Ser Pro Gly Val Gly Thr Glu Val Gln Gly Ala
         50                  55                  60

Leu Glu Arg Ser Leu Pro Glu Leu Gln Gln Ala Leu Ser Glu Leu Lys
 65                  70                  75                  80

Gln Ala Ser Ala Ala Arg Ala Val Gly Ala Gly Leu Ala Glu Val Phe
                 85                  90                  95

Gln Leu Val Glu Glu Ala Trp Leu Leu Pro Ala Val Gly Arg Glu Val
                100                 105                 110

Ala Gln Gly Leu Cys Asp Ala Ile Arg Leu Asp Gly Gly Leu Asp Leu
            115                 120                 125

Leu Leu Arg Leu Leu Gln Ala Pro Glu Leu Glu Thr Arg Val Gln Ala
        130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Lys His Ser Glu Glu Thr Cys Gln Arg Leu Val Ala Ala Gly Gly Leu
        195                 200                 205

Asp Ala Val Leu Tyr Trp Cys Arg Arg Thr Asp Pro Ala Leu Leu Arg
    210                 215                 220

His Cys Ala Leu Ala Leu Ala Asn Cys Ala Leu His Gly Gly Gln Thr
225                 230                 235                 240

Val Gln Arg Cys Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270

Ala Val Ala Val Leu Ala Thr Asn Lys Glu Val Glu Arg Glu Val Glu
        275                 280                 285

His Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320
```

```
Gly Arg Gly Pro Asp Asp Leu Gln Ser Leu Val Leu Leu Asp Ser
            325                 330                 335

Ser Arg Leu Glu Ala Gln Cys Ile Gly Ala Phe Tyr Leu Cys Ala Glu
        340                 345                 350

Ala Ala Ile Lys Ser Leu Gln Gly Lys Thr Lys Val Phe Ser Asp Ile
            355                 360                 365

Gly Ala Ile Gln Ser Leu Lys Arg Leu Val Ser Tyr Ser Thr Asn Gly
370                 375                 380

Thr Thr Ser Ala Leu Ala Lys Arg Ala Leu Arg Leu Gly Glu Glu
385                 390                 395             400

Val Pro Arg Arg Ile Leu Pro Cys Val Ala Ser Trp Lys Glu Ala Glu
                405                 410                 415

Val Gln Thr Trp Leu Gln Gln Ile Gly Phe Ser Gln Tyr Cys Glu Asn
            420                 425                 430

Phe Arg Glu Gln Gln Val Asp Gly Asp Leu Leu Leu Arg Leu Thr Asp
        435                 440                 445

Glu Glu Leu Gln Thr Asp Leu Gly Met Lys Ser Ser Ile Thr Arg Lys
            450                 455                 460

Arg Phe Phe Arg Glu Leu Thr Glu Leu Lys Thr Phe Ala Ser Tyr Ala
465                 470                 475                 480

Thr Cys Asp Arg Ser Asn Leu Ala Asp Trp Leu Gly Ser Leu Asp Pro
                485                 490                 495

Arg Phe Arg Gln Tyr Thr Tyr Gly Leu Val Ser Cys Gly Leu Asp Arg
            500                 505                 510

Ser Leu Leu His Arg Val Ser Glu Gln Gln Leu Leu Glu Asp Cys Gly
            515                 520                 525

Ile Arg Leu Gly Val His Arg Thr Arg Ile Leu Ser Ala Ala Arg Glu
530                 535                 540

Met Leu His Ser Pro Leu Pro Cys Thr Gly Gly Lys Leu Ser Gly Asp
545                 550                 555                 560

Thr Pro Asp Val Phe Ile Ser Tyr Arg Arg Asn Ser Gly Ser Gln Leu
                565                 570                 575

Ala Ser Leu Leu Lys Val His Leu Gln Leu His Gly Phe Ser Val Phe
            580                 585                 590

Ile Asp Val Glu Lys Leu Glu Ala Gly Lys Phe Glu Asp Lys Leu Ile
            595                 600                 605

Gln Ser Val Ile Ala Ala Arg Asn Phe Val Leu Val Leu Ser Ala Gly
            610                 615                 620

Ala Leu Asp Lys Cys Met Gln Asp His Asp Cys Lys Asp Trp Val His
625                 630                 635                 640

Lys Glu Ile Val Thr Ala Leu Ser Cys Gly Lys Asn Ile Val Pro Ile
                645                 650                 655

Ile Asp Gly Phe Glu Trp Pro Glu Pro Gln Ala Leu Pro Glu Asp Met
            660                 665                 670

Gln Ala Val Leu Thr Phe Asn Gly Ile Lys Trp Ser His Glu Tyr Gln
            675                 680                 685

Glu Ala Thr Ile Glu Lys Ile Ile Arg Phe Leu Gln Gly Arg Pro Ser
        690                 695                 700

Gln Asp Ser Ser Ala Gly Ser Asp Thr Ser Leu Glu Gly Ala Thr Pro
705                 710                 715                 720

Met Gly Leu Pro

<210> SEQ ID NO 7
```

```
<211> LENGTH: 42
<212> TYPE: DNA
<213> ORGANISM: Artificial Sequence
<220> FEATURE:
<223> OTHER INFORMATION: synthetically generated oligonucleotides

<400> SEQUENCE: 7
atatatatgc ggccgcaaaa catgggcaat cgtttgagcg gc                          42

<210> SEQ ID NO 8
<211> LENGTH: 20
<212> TYPE: DNA
<213> ORGANISM: Artificial Sequence
<220> FEATURE:
<223> OTHER INFORMATION: synthetically generated oligonucleotides

<400> SEQUENCE: 8
cgttagaacg cggctacaat                                                   20

<210> SEQ ID NO 9
<211> LENGTH: 127
<212> TYPE: DNA
<213> ORGANISM: Artificial Sequence
<220> FEATURE:
<223> OTHER INFORMATION: synthetically generated oligonucleotides

<400> SEQUENCE: 9
agatactcga gttaccaaaa tatcatgcgc ccggcattgg gggaggtggc cttggacaga        60
atgatgcccg aaagttcctc gtcctccatt tcgttgtttt ttatcagcga gcggaccttc       120
ttcatcg                                                                127

<210> SEQ ID NO 10
<211> LENGTH: 36
<212> TYPE: DNA
<213> ORGANISM: Artificial Sequence
<220> FEATURE:
<223> OTHER INFORMATION: synthetically generated oligonucleotides

<400> SEQUENCE: 10
gatcactagt ccaaaatatc atgcgcccgg cattgg                                 36
```

THERAPEUTIC APPLICATIONS TARGETING SARM1

CLAIM OF PRIORITY

This application is a divisional and claims priority to U.S. patent application Ser. No. 13/530,998, filed on Jun. 22, 2012, which claims the benefit of U.S. Provisional Patent Application Ser. No. 61/501,111, filed on Jun. 24, 2011, the entire contents of which are hereby incorporated by reference.

FEDERALLY SPONSORED RESEARCH OR DEVELOPMENT

This invention was made with Government support under Grant Nos. R01 NS059991, U54NS065712, and R01NS072248, awarded by the National Institutes of Health. The Government has certain rights in the invention.

TECHNICAL FIELD

The present disclosure relates to compositions and methods for modulating sterile α/Armadillo/Toll-Interleukin receptor homology domain protein (SARM1) for use in the treatment of neurological disorders that manifest and/or include axonal and/or synaptic degradation (e.g., neurodegenerative disorders).

BACKGROUND

Widespread axonal and synaptic degeneration is a hallmark of peripheral neuropathy, brain injury, and neurodegenerative disease. Neurodegeneration and neurodegenerative disorders include progressive structural and/or functional loss of nerve cells or neurons in the peripheral nervous system (PNS) and/or central nervous system (CNS). Axon degeneration has been proposed to be mediated by an active auto-destruction program, akin to apoptotic cell death, however loss of function mutations capable of potently blocking axon self-destruction have not been described.

Axons have traditionally been thought to be strictly dependent upon the cell body for survival, as axons robustly degenerate upon separation from the soma (Waller, Philos. Trans. R. Soc. Lond. B Biol. Sci. 140, 423 (1850)). However, this notion was directly challenged by the identification of the slow Wallerian degeneration (Wld$^s$) mutant mouse in which the distal portion of severed axons remained morphologically intact for 2-3 weeks after axotomy (Lunn et al., Eur J Neurosci 1, 27 (1989); Glass et al., J Neurocytol 22, 311 (1993)). The remarkable long-term survival of severed axons in the Wld$^S$ mouse also raised the intriguing possibility that Wallerian degeneration is driven by an active molecular program akin to apoptotic cell death signaling (Raff et al., Science 296, 868 (2002); Coleman and Perry, Trends Neurosci 25, 532 (2002)). However numerous studies have demonstrated that Wld$^S$ is a gain-of-function mutation that results in the neuronal overexpression of a chimeric fusion protein containing the NAD$^+$ biosynthetic enzyme Nmnat1 (Mack et al., Nat Neurosci 4, 1199 (2001); Coleman and Freeman, Annu Rev Neurosci 33, 245 (2010)). As such, the Wld$^S$ phenotype may be unrelated to normal Nmnat1 function and NAD$^+$ metabolism, despite its ability to inhibit endogenous axon death pathways. Wallerian degeneration appears to be molecularly distinct from apoptosis since potent genetic or chemical inhibitors of cell death (Deckwerth and Johnson, Jr., Dev Biol 165, 63 (1994); Finn et al., J Neurosci 20, 1333 (2000); Whitmore et al., Cell Death Differ 10, 260 (2003)) or the ubiquitin proteasome pathway (Zhai et al., Neuron 39, 217 (2003); Hoopfer et al., Neuron 50, 883 (2006)) do not block Wallerian degeneration. Mutants reported to affect Wallerian degeneration, such as wnd/DLK, delay the clearance of degenerating axons in *Drosophila* for only ~1-2 days, and mouse axons for several hours (Miller et al., Nat Neurosci 12, 387 (2009))—an extremely weak degree of suppression when compared to Wld$^S$. Thus the existence of axon death pathways has remained only speculative. Compositions and methods for treating neurodegeneration and neurodegenerative disorders in the PNS and CNS are needed.

SUMMARY

The present disclosure provides compositions and methods related to the modulation (e.g., inhibition) of SARM expression and/or activity for the treatment of neurodegeneration that manifests and/or includes axonal and/or synaptic degradation in a subject.

In some aspects, the disclosure provides methods for reducing axonal and/or synaptic degradation in a neuron. Such methods can include selecting, providing, or obtaining a neuron with, undergoing, or at risk for axonal and/or synaptic degradation, and contacting or treating the neuron with an effective amount of a composition that inhibits sterile α/Armadillo/Toll-Interleukin receptor homology domain protein (SARM) activity and/or expression for a time sufficient to inhibit SARM activity and/or expression, thereby reducing axonal and/or synaptic degradation in the neuron. In some embodiments, these methods are performed in vitro. In other embodiments, the methods are performed in vivo.

In other aspects, the disclosure provides methods for reducing axonal and/or synaptic degradation in a subject with or at risk for developing axonal and/or synaptic degradation, for example, in the central and/or peripheral nervous system. Such methods can include selecting a subject with or at risk for developing axonal and/or synaptic degradation, and treating the subject with, or administering to the subject, an effective amount or dose of a composition that inhibits SARM activity and/or expression, thereby reducing axonal and/or synaptic degradation in the subject. In some embodiments, subjects suitable for treatment can have or be at risk of developing neurodegenerative disease. In addition, such subjects can have or be at risk of developing axonal and/or synaptic degradation is in the central and/or peripheral nervous system. In some embodiments, a subject with or at risk of developing axonal and/or synaptic degradation can have diabetes and/or diabetic neuropathy (e.g., peripheral neuropathy). Alternatively or in addition, the subject can be scheduled to receive chemotherapy, undergoing chemotherapy, and or have previously had chemotherapy.

In further aspects, the disclosure includes methods for identifying compounds that inhibit SARM activity and/or expression. Such methods can include providing or obtaining a sample containing SARM, contacting the sample or SARM with a compound (e.g., a test compound), and determining whether the test compound interacts with or binds to SARM, wherein a compound that interacts or binds with SARM is a candidate compound that inhibits SARM activity and/or expression. In some embodiments, such methods are performed entirely or partially in silico or bioinformatically, e.g., via modeling. In other instances, the methods are performed in vitro. For example, SARM (e.g., isolated SARM, portions or SARM, or isolated SARM domains) are physically contacted with the test compound. Either way, the methods can include determining whether the compound interacts with or binds to SARM directly, e.g., by assessing the interaction of SARM and the compound in the absence of other components. Alternatively or in addition, the methods can include determining whether the compound interacts with or binds to SARM indirectly, for example, using a component in addition to SARM and the test compound, wherein the additional component binds to SARM in the absence of the compound, and wherein this binding of the compound to SARM is reduced by a test compound that also binds to SARM.

In yet further aspects, the disclosure includes methods for identifying compounds that inhibit SARM activity and/or expression that involve providing or obtaining a sample containing SARM, contacting the sample containing SARM with a test compound, and measuring the transcriptional activity of SARM, wherein a decrease in the transcriptional activity of SARM in the presence of the compound indicates that the compound is a candidate compound that inhibits SARM activity and/or expression. Measuring the transcriptional activity of SARM can include measuring SARM transcriptional activity (e.g., using a genetic reporter construct containing a SARM promoter, or a biologically active portion of a SARM promoter, operably linked to a reporter, such as a nucleic acid sequence encoding a detectable protein (e.g., a fluorescent protein (e.g., green fluorescent protein) or an enzyme, such as luciferase (e.g., firefly luciferase)). Such methods can be high-throughput.

In additional aspects, the disclosure includes methods for identifying compounds that inhibit SARM activity and/or expression that involve contacting or treating a neuron (e.g., a cultured neuron) with a candidate compound identified via the in silico or in vitro methods disclosed herein, e.g., to confirm that the candidate compound reduces axonal and/or synaptic degradation in injured neurons. In other embodiments, compounds applied in such methods are not first identified via the in silico or in vitro methods disclosed herein. Either way, the methods can include injuring the neuron, for example, by axotomizing the neuron, and determining whether axonal and/or synaptic degradation is altered in the presence of the candidate compound relative to axonal degradation in the absence of the compound, wherein a decrease in axonal and/or synaptic degradation indicates that the candidate compound is a compound that inhibits SARM activity and/or expression. In some embodiments, the neuron is contacted or treated with the compound before injury. In other embodiments, the neuron is contacted or treated with the compound after injury.

In other aspects, the disclosure includes administering a compound to an animal model of neurodegenerative disease to allow assessment or verification of whether the compound can be used to treat neurodegenerative disease and/or whether the compound inhibits SARM activity and/or expression in the animal model.

Any of the methods for identifying compounds that modulate SARM can include, where appropriate, conducting control experiments to confirm positive observation and/or to identify and/or exclude false positives.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-I. Identification of three mutations that suppress Wallerian degeneration in vivo.

Figure 1A:
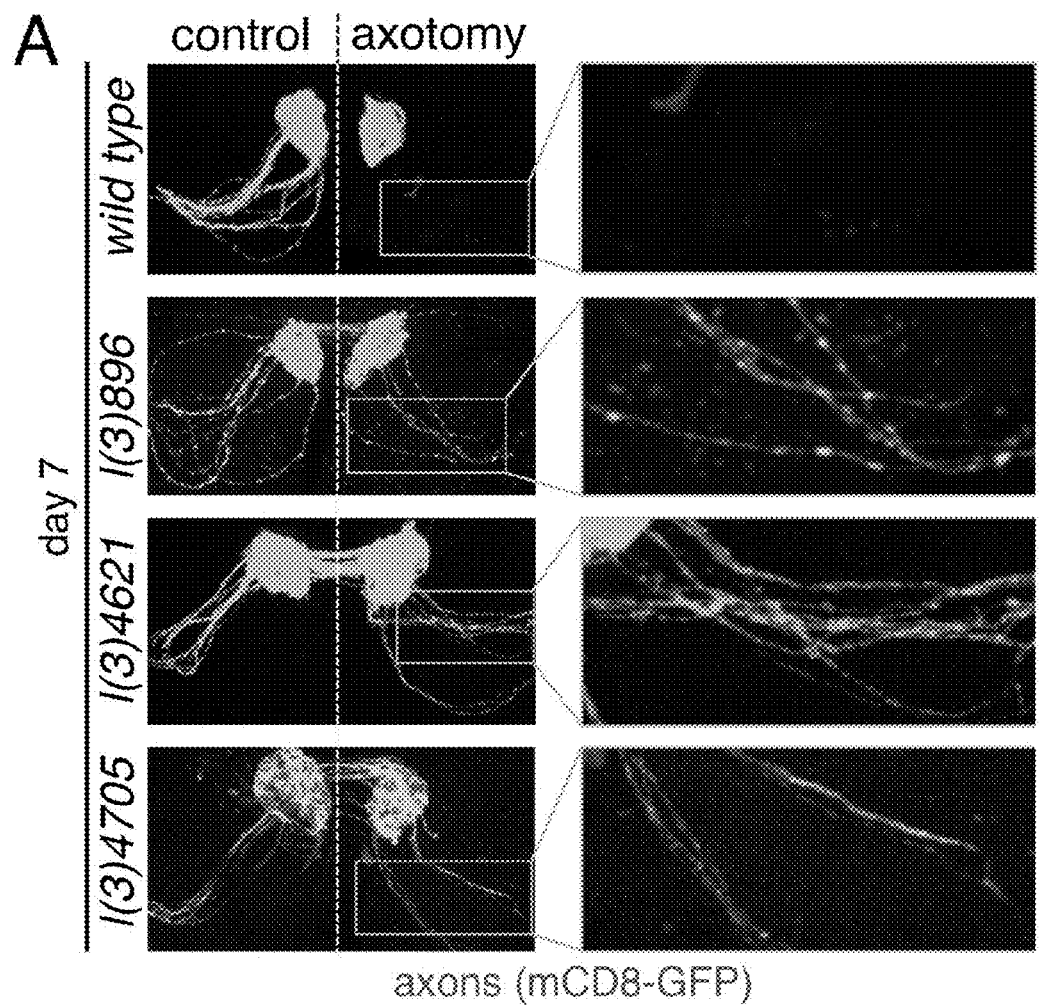

A. ORN MARCM clones in control, l(3)896, l(3)4621, and l(3)4705. Right, axotomy; left, uninjured control. Boxed regions are enlarged at right. n≥15.

B. Control and l(3)896 brains 30 days after injury. n≥10.

C. l(3)896 clones 50 days after injury. n=11.

D. Control ORN MARCM clones labeled with UAS-nSyb::GFP, uninjured (top) and 30 days after axotomy (bottom). n≥15.

E. l(3)896 MARCM clones labeled with UAS-nSyb::GFP, uninjured (top) and 30 days after axotomy (bottom). n≥15.

F. MARCM clones in mushroom body (MB) γ neurons in control and l(3)896 backgrounds at the indicated developmental stages. dorsal (d) and medial (m) axonal branches (arrows), and dendrites (circled). n≥15 for all.

G. dMP2 neurons with GFP. Ventral views (anterior up) of stage 16 embryos (left) and $1^{st}$ instar larvae. dMP2 neurons before (arrows) and after (arrowheads) segment-specific apoptosis. n≥20 at each time point.

H. Wild type and l(3)896 mutant clones with (right) or without (left) ectopic expression of hid. n≥20.

I. Wild type and l(3)896 mutant clones in the eye-antennal disc of $3^{rd}$ instar larvae. Homozygous mutant clones are labeled as GFP-negative (circled). Red, TUNEL staining n≥10.

FIGS. 2A-D. Mutations in dsarm block Wallerian degeneration

A. The lethality of l(3)896, l(3)4621, and l(3)4705 was mapped to region 66B.

B. The locations of the point mutations in dsarm that block axon degeneration and their corresponding resulting protein change.

C. Dsarm protein domains, positions and effect of predicted point mutations.

D. UAS-dsarm in l(3)896 mutant clones or a dsarm⁺ BAC rescue axonal degeneration defects in l(3)896/l(3)4621 animals. n=12.

FIGS. 3A-H. Sarm1−/− primary cultures are protected from Wallerian degeneration but not NGF withdrawal-induced axonal degeneration.

A. Phase contrast images of SCG explant cultures from wild type (top), Sarm−/− (middle), and Wld$^s$ expressing (bottom) animals at the indicated time after axotomy.

B. Quantification from A. Mean±SEM, *p<0.01.

C. Axon preservation at the indicated time points in cortical neuron cultures from E16.5 mouse embryos. a-Tau, red.

D. Quantification from C. Mean±SEM, *p<0.01.

E. Axon preservation at the indicated time points in DRG cultures from E13.5 mouse embryos. a-TUJI, green.

F. Quantification from E. Mean±SEM, *p<0.01.

G. DRG explant cultures from E13.5 mouse embryos after NGF withdrawal at the indicated time points. a-TUJI, green.

H. Quantification from G Mean±SEM, *p<0.01.

FIGS. 4A-F. Sarm1 is required for Wallerian degeneration in mice in vivo

A. Sciatic nerve distal to the injury site stained with Toludine blue. Time points and genotypes as indicated.

B. Ultra-structural analysis of Sarm+/− and Sarm−/− axons before or 14 days after axotomy. my, myelin; nf, neurofilaments, m, mitochondrion.

C. NMJ preservation at tibialis anterior muscles. red, AChR (post synapse/muscle); green, NF-M/synpatophysin (presynapse).

D. Immunoblot analysis of distal injured nerve segment. n=4 at each timepoint and genotype.

E. Quantification from A. n=5 for all. (p=0.0002)

F. Quantification from C. n>200 synapses for each genotype and time point.

FIGS. 5A-B. Crossing schemes for EMS mutant lines and generating MARCM lines for screening A. Crossing scheme for generating a collection of ~2000 mutant stocks, each with a unique EMS-mutagenized third chromosome containing FRT sites on each arm.

B. Scheme for generating MARCM clones and screening mutants for phenotypes in OR22a-positive neurons using ey-flp.

Figure 6A:
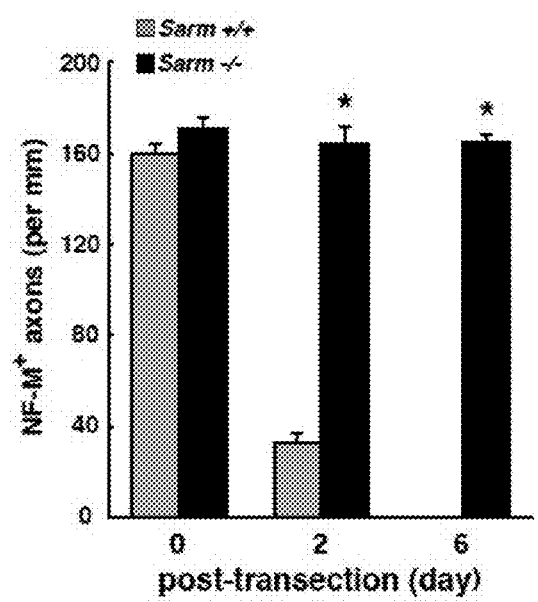
Figure 6B:
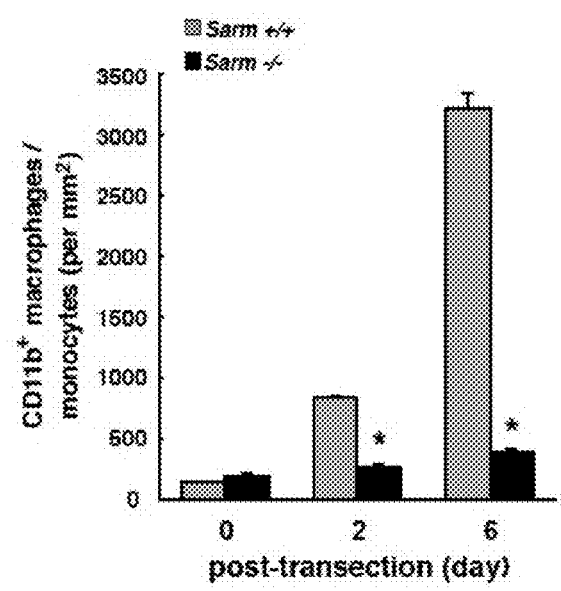

FIGS. 6A-B. Sarm1 knockout mice are protected from axon degeneration after sciatic nerve lesion in vivo Right sciatic nerves were lesioned in 6-8 week old Sarm1−/− or Sarm1+/+ mice.

A. Transected nerves were stained for neurofilament-M as a marker of structure integrity of the injured axon at the indicated time points. n=4 mice for all. Values are presented as mean±SEM, *p<0.01.

B. Macrophage/monocyte infiltration into transected nerves was assayed by staining for CD11b (macrophages) and DAPI (all cells) at the indicated time points after lesion. n=4 mice for all. Values are presented as mean±SEM, *p<0.01.

DETAILED DESCRIPTION

The present disclosure is based, inter alia, on the surprising discovery that the Drosophila Toll receptor adaptor dSarm (sterile α/Armadillo/Toll-Interleukin receptor homology domain protein) promotes axon destruction, and that loss of dSarm function can cell-autonomously suppress the degeneration of severed axons for the lifespan of the fly. Pro-degenerative Sarm1 function is conserved in mice, where transected Sarm1 null axons exhibit remarkable long-term survival both in vivo and in vitro. Neurons undergoing axonal and/or synaptic degradation (e.g., a process known as Wallerian degeneration) benefit from the modulation (e.g., inhibition) of Sterile α and HEAT/Armadillo Motifs Containing Protein (SARM, also commonly referred to in the art as MyD88-5) expression and/or function. Specifically, injured neurons show reduced axonal and synaptic degradation (e.g., Wallerian degeneration) following injury (axotomy) when SARM is reduced in the neuron. Furthermore, Wallerian degeneration in injured neurons was apparently halted in injured neurons leading to axonal and/or synaptic repair. Accordingly, the present disclosure provides compositions and methods for treating a subject with or at risk of a neurological disorder that manifests and/or includes axonal and/or synaptic degradation (e.g., Wallerian degeneration) by targeting and thereby modulating (e.g., inhibiting) SARM (e.g., SARM1) to reduce axonal and/or synaptic degradation in the subject.

Data leading to the present disclosure includes generation and functional analysis of four distinct loss-of-function genetic mutations that maintain, improve, or enhance the structure and/or function of axons and/or synapses post axonal injury in Drospophila. As shown herein, each of the four mutations map to the Drosophila homologue of mammalian SARM (SARM1), dSARM.

dSarm is reportedly most similar to mammalian SARM, SARM1 (Mink et al., Genomics, 74:234-244, 2001). A single SARM gene has been identified in Caenorhabditis elegans, Drosophila, mouse, and human and its sequence is conserved among these species. SARM is generally functionally associated with the host immune response. Specifically, SARM is reported to be negative regulator of Toll receptor signaling (O'Neil et al., Trends Immunol., 24:286-290, 2003). Reports also describe a functional role of SARM in the regulation of neuronal survival/death. For example, murine SARM is reportedly predominantly expressed in neurons and is involved in the regulation of neuronal death in response to oxygen glucose deprivation and exposure of neurons to the Parkinsonian neurotoxin 1-methyl-4-phenyl-1,2,3,6-tetrahydropyridine (MPTP) (Kim et al., JEM, 204: 2063-2074, 2007 and Kim et al., Abstract from the Toll2008 meeting conducted in Lisbon, Portugal from Sep. 24-27, 2008, entitled Distinctive role of MyD88-5 (SARM) in neurodegeneration and host defense). A role for SARM has also been described in neuronal development (Yuan et al., J. Immunol., 184:6874-6881, 2010). Reviews on this subject are available (see, e.g., Dalod, Science Signaling, 417:1-3, 2007).

Compositions and Methods for Modulating SARM

The disclosure includes compositions and methods for modulating (e.g., inhibiting) SARM expression (e.g., protein and/or nucleic acid (mRNA) expression) and/or activity (e.g., protein activity). Such compositions and methods generally include targeting (e.g., specifically targeting) SARM DNA, mRNA, and/or protein to thereby modulate (e.g., inhibit) SARM mRNA and/or protein expression and/or function. In some instances, targeting (e.g., specifically targeting) SARM can include targeting (e.g., specifically targeting) SARM in a neuron (including in the neuronal cell body), in an axon, in a synapse, and/or in a dendrite. SARM can additionally be targeted in non-neuronal cells, including cells of the immune system, as long as SARM is targeted in a neuron (including in the neuronal cell body), in an axon, in a synapse, and/or in a dendrite.

SARM included in the present disclosure includes C. elegans, Drosophila, and mammalian (e.g., mouse and human (e.g., SARM1)) SARM DNA, mRNA, and/or protein, including full length transcripts and proteins, truncated transcripts and proteins (e.g., truncated SARM transcripts and proteins that exhibit or have detectable SARM activity), and/or mutant or mutated SARM transcripts and protein, truncated or otherwise (e.g., that exhibit or have detectable SARM activity). The term SARM also refers to and includes synonyms of SARM (synonyms can be viewed at, e.g., ihop-net.org).

In some instances, SARM can include SEQ ID NO:1 (human SARM1 mRNA (national center for biotechnology information (NCBI) accession number NM_015077 (NM_015077.2)); SEQ ID NO:2 (human SARM1 protein (NCBI accession number NP_055892 (NP_055892.2)); SEQ ID NO:3 (murine SARM1 mRNA, isoform 1 (NCBI accession number NM_001168521 (NM_001168521.1));

SEQ ID NO:4 (murine SARM1 protein, isoform 1 (NCBI accession number NP_001161993 (NP_001161993.1)); SEQ ID NO:5 (murine SARM1 mRNA, isoform 2 (NCBI accession number NM_172795 (NM_172795.3)); and/or SEQ ID NO:6 (murine SARM1 protein, isoform 2 (NCBI accession number NP_766383 (NP_766383.2)). Accordingly, the present disclosure provides compositions and methods for treating a subject with or at risk of a neurological disorder that manifests and/or includes axonal and/or synaptic degradation by targeting (e.g., specifically targeting) one or more of SEQ ID NOs: 1, 2, 3, 4, 5, and/or 6 in a neuron (including in the neuronal cell body), in an axon, in a synapse, and/or in a dendrite, thereby modulating (e.g., inhibiting) SARM (e.g., SARM1) to reduce axonal and/or synaptic degradation in the subject.

SARM can also include SARM-like nucleic acid and amino acid sequences with certain percent identity to SEQ ID NOs: 1, 2, 3, 4, 5, and/or 6. Suitable identity can include, for example, 50%, 60%, 70%, 80%, 85%, 90%, 95%, 98%, 99%, and 100% identity between SEQ ID NOs: 1, 2, 3, 4, 5, and/or 6 and the SARM-like sequence.

Methods for determining percent identity between nucleic acid and amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

Compositions for modulating SARM expression and/or activity can include, but are not limited to, one or more of: small molecules, inhibitory nucleic acids, antibodies, and inhibitory peptides. For example, one or more of a small molecule, an inhibitory nucleic acid, an anti-SARM antibody, and/or an inhibitory nucleic acid can be used to target (e.g., specifically target) SARM (e.g., SEQ ID NOs: 1, 2, 3, 4, 5, and/or 6) in a neuron (including in the neuronal cell body), in an axon, in a synapse, and/or in a dendrite, thereby modulating (e.g., inhibiting) SARM (e.g., SARM1) to reduce axonal and/or synaptic degradation in the subject.

Small Molecules

Suitable small molecules include small molecules that inhibit SARM expression and/or activity directly, indirectly, or both directly and indirectly. Suitable small molecules include small molecules that bind (e.g., bind specifically) to SARM and thereby inhibit SARM expression and/or activity, and/or small molecules that do not bind to SARM or that bind to SARM with low affinity, but that inhibit SARM expression and/or activity by binding to a component of the SARM signaling pathway upstream or downstream of SARM.

Inhibitory Nucleic Acids

Inhibitory Nucleic Acids suitable for use in the methods described herein include inhibitory nucleic acids that bind (e.g., bind specifically) to SARM. Also encompassed are inhibitory nucleic acids that bind (e.g., bind specifically) to a component of the SARM signaling pathway upstream or downstream of SARM. Exemplary inhibitory nucleic acids include, but are not limited to, siRNA and antisense nucleic acids. For example, the disclosure includes siRNA and antisense nucleic acids that target or bind (e.g., specifically target or specifically bind) to SARM mRNA (e.g., SEQ ID NOs: 1, 3, and/or 5 and/or a nucleic acid sequence encoding SEQ ID NOs: 2, 4, or 6) in a neuron (including in the neuronal cell body), in an axon, in a synapse, and/or in a dendrite, thereby modulating (e.g., inhibiting) SARM (e.g., SARM1) to reduce axonal and/or synaptic degradation in the subject.

RNAi is a process whereby double-stranded RNA (dsRNA, also referred to herein as siRNAs or ds siRNAs, for double-stranded small interfering RNAs), induces the sequence-specific degradation of homologous mRNA in animals and plant cells (Hutvagner and Zamore, Curr. Opin. Genet. Dev.: 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al, Mol. Cell. 10:549-561 (2002); Elbashir et al, Nature 411:494-498 (2001)), or by micro-RNAs (miRNA), functional small-hairpin RNA (shRNA), or other dsRNAs which are expressed in vivo using DNA templates with RNA polymerase III promoters (Zeng et al, Mol. Cell 9: 1327-1333 (2002); Paddison et al, Genes Dev. 16:948-958 (2002); Lee et al, Nature Biotechnol. 20:500-505 (2002); Paul et al, Nature Biotechnol. 20:505-508 (2002); Tuschl, T., Nature Biotechnol. 20:440-448 (2002); Yu et al, Proc. Natl. Acad. Sci. USA 99(9):6047-6052 (2002); McManus et al, RNA 8:842-850 (2002); Sui et al, Proc. Natl. Acad. Sci. USA 99(6):5515-5520 (2002)).

RNAi useful for inhibiting SARM can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can be transcribed in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA Inhibitory nucleic acids can include both siRNA and modified siRNA derivatives, e.g., siRNAs modified to alter a property such as the pharmacokinetics of the composition, for example, to increase half-life in the body, as well as engineered RNAi precursors.

siRNA can be delivered into cells by methods known in the art, e.g., cationic liposome transfection and electroporation. Direct delivery of siRNA in saline or other excipients can silence target genes in tissues, such as the eye, lung, and central nervous system (Bitko et al., Nat. Med. 11:50-55 (2005); Shen et al., Gene Ther. 13:225-234 (2006); Thakker, et al., Proc. Natl. Acad. Sci. U.S.A. (2004)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)). Liposomes and nanoparticles can also be used to deliver siRNA into animals. Delivery methods using liposomes, e.g. stable nucleic acid-lipid particles (SNALPs), dioleoyl phosphatidylcholine (DOPC)-based delivery system, as well as lipoplexes, e.g. Lipofectamine 2000, TransIT-TKO, have been shown to effectively repress target mRNA (de Fougerolles, Human Gene Ther. 19:125-132 (2008); Landen et al., Cancer Res. 65:6910-6918 (2005); Luo et al., Mol. Pain. 1:29 (2005); Zimmermann et al., Nature 441:111-114 (2006)). Conjugating siRNA to peptides, RNA aptamers, antibodies, or polymers, e.g. dynamic polyconjugates, cyclodextrin-based nanoparticles, atelocollagen, and chitosan, can improve siRNA stability and/or uptake. (Howard et al., Mol. Ther. 14:476-484 (2006); Hu-Lieskovan et al., Cancer Res. 65:8984-8992 (2005); Kumar, et al., Nature 448:39-43; McNamara et al., Nat. Biotechnol. 24:1005-1015 (2007); Rozema et al., Proc. Natl. Acad. Sci. U.S.A. 104: 12982-12987 (2007); Song et al., Nat. Biotechnol. 23:709-717 (2005); Soutschek (2004), supra; Wolfium et al., Nat. Biotechnol. 25:1149-1157 (2007)). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., Proc. Natl. Acad. Sci. USA 99(22):14236-40 (2002)).

siRNA duplexes can be expressed within cells from engineered RNAi precursors, e.g., recombinant DNA constructs using mammalian Pol III promoter systems (e.g., HI or U6/snRNA promoter systems (Tuschl (2002), supra) capable of expressing functional double-stranded siRNAs; (Bagella et al, J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by HI or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

Synthetic siRNAs can be delivered into cells, e.g., by direct delivery, cationic liposome transfection, and electroporation. However, these exogenous siRNA typically only show short term persistence of the silencing effect (4.about.5 days). Several strategies for expressing siRNA duplexes within cells from recombinant DNA constructs allow longer-term target gene suppression in cells, including mammalian Pol II and III promoter systems (e.g., H1, U1, or U6/snRNA promoter systems (Denti et al. (2004), supra; Tuschl (2002), supra); capable of expressing functional double-stranded siRNAs (Bagella et al., J. Cell. Physiol. 177:206-213 (1998); Lee et al. (2002), supra; Miyagishi et al. (2002), supra; Paul et al. (2002), supra; Scherer et al. (2007), supra; Yu et al. (2002), supra; Sui et al. (2002), supra).

Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

siRNA can also be expressed in a miRNA backbone which can be transcribed by either RNA Pol II or III. MicroRNAs are endogenous noncoding RNAs of approximately 22 nucleotides in animals and plants that can post-transcriptionally regulate gene expression (Bartel, *Cell* 116: 281-297 (2004); Valencia-Sanchez et al., Genes & Dev. 20:515-524 (2006)). One common feature of miRNAs is that they are excised from an approximately 70 nucleotide precursor RNA stem loop by Dicer, an RNase III enzyme, or a homolog thereof. By substituting the stem sequences of the miRNA precursor with the sequence complementary to the target mRNA, a vector construct can be designed to produce siRNAs to initiate RNAi against specific mRNA targets in mammalian cells. When expressed by DNA vectors containing polymerase II or III promoters, miRNA designed hairpins can silence gene expression (McManus (2002), supra; Zeng (2002), supra).

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage, destabilization, and/or translation inhibition destruction. In this fashion, the mRNA to be targeted by the siRNA generated from the engineered RNA precursor will be depleted from the cell or organism, leading to a decrease in the concentration of the protein encoded by that mRNA in the cell or organism.

An "antisense" nucleic acid can include a nucleotide sequence that is complementary to a "sense" nucleic acid encoding a protein, e.g., complementary to the coding strand of a double-stranded cDNA molecule or complementary to a PKCd mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested. Such methods can also be used to identify siRNAs.

In some embodiments, the antisense nucleic acid molecule is a cc-anomeric nucleic acid molecule. A cc-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243:209-14 (2002); Iversen, Curr. Opin. Mol. Ther. 3:235-8 (2001); Summerton, Biochim. Biophys. Acta. 1489: 141-58 (1999).

Target gene expression can be inhibited by targeting nucleotide sequences complementary to a regulatory region (e.g., promoters and/or enhancers) to form triple helical structures that prevent transcription of the Spt5 gene in target cells. See generally, Helene, Anticancer Drug Des. 6:569-84 (1991); Helene, C. Ann. N.Y. Acad. Sci. 660:27-36 (1992); and Maher, Bioassays 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Antisense nucleic acid molecules of the invention can be administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

Additional information regarding antisense technologies and their use in vivo can be found in Crooke, Antisense Drug Technology: Principles, Strategies and Applications, (CRC Press, 2007).

Locked Nucleic Acids

LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to block mRNA translation.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the lncRNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target lncRNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the LNA molecules can be designed to target a specific region of the lncRNA. For example, a specific functional region can be targeted, e.g., a region comprising a known RNA localization motif (i.e., a region complementary to the target nucleic acid on which the lncRNA acts), or a region comprising a known protein binding region, e.g., a Polycomb (e.g., Polycomb Repressive Complex 2 (PRC2), comprised of H3K27 methylase EZH2, SUZ12, and EED)) or LSD1/CoREST/REST complex binding region (see, e.g., Tsai et al., Science. 2010 Aug. 6; 329(5992):689-93. Epub 2010 Jul. 8; and Zhao et al., Science. 2008 Oct. 31; 322(5902):750-6). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

For additional information regarding LNAs see U.S. Pat. Nos. 6,268,490; 6,734,291; 6,770,748; 6,794,499; 7,034, 133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Ribozymes

Ribozymes suitable for use in methods encompassed by the present disclosure include ribozymes that recognize and/or cleave SARM and/or components of the SARM signaling pathway upstream or downstream of SARM. For example, the disclosure includes ribozymes that recognize and/or cleave SARM mRNA (e.g., SEQ ID NOs: 1, 3, and/or 5 and/or a nucleic acid sequence encoding SEQ ID NOs: 2, 4, or 6) in a neuron (including in the neuronal cell body), in an axon, in a synapse, and/or in a dendrite, thereby modulating (e.g., inhibiting) SARM (e.g., SARM1) to reduce axonal and/or synaptic degradation in the subject.

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a cDNA described herein, and a sequence having known catalytic sequence responsible for mRNA cleavage (see U.S. Pat. No. 5,093, 246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA (Cech et al. U.S. Pat. No. 4,987,071; and Cech et al. U.S. Pat. No. 5,116,742). Alternatively, target mRNA can be used to select a catalytic RNA having a specific ribonuclease activity from a pool of RNA molecules (Bartel and Szostak, Science 261: 1411-1418 (1993)).

Aptamers

Aptamers suitable for use in methods encompassed by the present disclosure include aptamers that bind (e.g., bind specifically) to SARM and/or components of the SARM signaling pathway upstream or downstream of SARM. For example, the disclosure includes aptamers that bind (e.g., bind specifically) to SARM amino acid sequences (e.g., SEQ ID NOs: 2, 4, and/or 6) in a neuron (including in the neuronal cell body), in an axon, in a synapse, and/or in a dendrite, thereby modulating (e.g., inhibiting) SARM (e.g., SARM1) to reduce axonal and/or synaptic degradation in the subject.

Aptamers are short oligonucleotide sequences which can specifically bind specific proteins. It has been demonstrated that different aptameric sequences can bind specifically to different proteins, for example, the sequence GGNNGG where N=guanosine (G), cytosine (C), adenosine (A) or thymidine (T) binds specifically to thrombin (Bock et al (1992) Nature 355: 564 566 and U.S. Pat. No. 5,582,981 (1996) Toole et al). Methods for selection and preparation of such R A aptamers are knotn in the art (see, e.g., Famulok, Curr. Opin. Struct. Biol. 9:324 (1999); Herman and Patel, J. Science 287:820-825 (2000)); Kelly et al, J. Mol. Biol. 256:417 (1996); and Feigon et al, Chem. Biol. 3: 611 (1996)).

Antibodies

The present disclosure also includes methods that include the use or administration of antibodies and antibody fragments that bind (e.g., bind specifically) to SARM (e.g., SEQ ID NOs: 2, 4, and or 6 and/or an epitope presented on native SARM (e.g., SEQ ID NOs: 2, 4, and or 6)) and thereby inhibit SARM activity in a neuron. Antibodies and antibody fragments that bind (e.g., bind specifically) epitopes expressed (e.g., specifically expressed) on the surface of a neuron such that when the epitope is bound by the antibody SARM expression and/or activity is reduced are also included in the present disclosure.

Inhibitory Peptides

Also included in the present disclosure are methods that include the use or administration of inhibitory peptides that bind (e.g., bind specifically) to SARM or interact with SARM and thereby inhibit SARM activity and/or expression in a neuron. Such peptides can bind or interact with an epitope on SARM and/or with a SARM domain. SARM domains that can be bound by inhibitory peptides include, but are not limited to, the alpha helical domain (e.g., including the interacting face of the SARM α helix) and/or the TIR domain. Suitable inhibitory peptides can that bind or interact with SARM can also be used to increase SARM degradation, for example, by increasing ubiquitination and/ or proteosomal degradation of SARM.

Antibodies and inhibitory peptides can be modified to facilitate cellular uptake or increase in vivo stability. For example, acylation or PEGylation facilitates cellular uptake, increases bioavailability, increases blood circulation, alters pharmacokinetics, decreases immunogenicity and/or decreases the needed frequency of administration.

Methods for synthesizing suitable peptides are known in the art. For example, the peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH2 protected by either t-Boc or Fmoc chemistry using side chain protected amino acids on, for example, an Applied Biosystems Peptide Synthesizer Model 430A or 431.

The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome.

Effective amounts of one or more compounds or a pharmaceutical composition for use in the present invention include amounts that inhibit SARM expression, levels (e.g., protein levels) and/or activity (e.g., biological activity) in neurons. An effective amount can also include an amount that inhibits or prevents Wallerian degeneration (e.g., axonal and/or synaptic degradation) in a neuron. For example, in the treatment of neurodegeneration, an effective amount of a compound includes a compound in an amount that improves to any degree or arrests any symptom of the disease. A therapeutically effective amount of a compound is not required to cure a disease but will provide a treatment for a disease.

In some embodiments, the present disclosure provides methods for using any one or more of the compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

Pharmaceutical Compositions

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include systemic and local routes of administration. Exemplary routes include, but are not limited to, parenteral, e.g., intravenous, intradermal, subcutaneous, oral (e.g., inhalation), transdermal (topical), and transmucosal, administration. Methods of formulating suitable pharmaceutical compositions for each of these routes of administration are known in the art, see, e.g., the books in the series Drugs and the Pharmaceutical Sciences: a Series of Textbooks and Monographs (Dekker, NY).

The pharmaceutical compositions can be included in a container, pack, or dispenser together with instructions for administration Dosage Effective amounts are discussed above. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Pharmaceutical Compositions and Methods of Administration Methods of Treatment/Personalized Medicine The disclosure includes methods for treating a subject with or at risk of a neurological disorder that manifests and/or includes axonal and/or synaptic degradation (e.g., Wallerian degeneration) with a composition disclosed herein to target and thereby modulate (e.g., inhibit) SARM (e.g., SARM1) to reduce axonal and/or synaptic degradation in the subject.

As used herein, "treatment" means any manner in which one or more of the symptoms of a disease or disorder disclosed herein are ameliorated or otherwise beneficially altered. As used herein, amelioration of the symptoms of a particular disorder refers to any lessening, whether permanent or temporary, lasting or transient that can be attributed to or associated with treatment by the compositions and methods of the present invention. In some embodiments, treatment can promote or result in, for example, a decrease in the level or rate of axonal and/or synaptic degradation (e.g., Wallerian degeneration) in the subject relative to the level or rate prior to treatment; and/or reductions in one or more symptoms (e.g., a reduction in the severity of the symptoms) associated with the subject's disease in the subject relative to the subject's symptoms prior to treatment.

As mentioned above, neurodegeneration and neurodegenerative disorders include progressive structural and/or functional loss of nerve cells or neurons in the peripheral nervous system (PNS) and/or central nervous system (CNS). Many degenerative diseases or conditions are known to manifest and/or include axonal and/or synaptic degradation (e.g., Wallerian degeneration) and each of these diseases is suitable for treatment using the compositions and methods disclosed herein. Examples of neurodegenerative diseases that can be treated using the compositions and methods disclosed herein include, but are not limited to, the classes of disease: central nervous system (CNS) disorders, peripheral nervous system (PNS) disorders, trauma-related disorders (including trauma to the head, the spine, and/or the PNS), genetic disorders, metabolic and/or endocrine related disorders (e.g., peripheral neuropathy in diabetes), toxin-related disorders (e.g., peripheral neuropathy induced by toxins (including chemotherapeutic agents)), inflammatory disease, exposure to excess vitamin, vitamin deficiency, and cardiovascular-related disorders (e.g., stroke). Examples of these classes include, but are not limited to, the following diseases and/or causes of disease: Huntington's disease, Alzheimer's disease, Parkinson's disease, Amyotrophic lateral sclerosis (ALS)), axonal abnormalities (e.g., Wallerian degeneration), age-related neurodegeneration (including, for example, dementia), dementia pugilistica (or so called 'punch drunk syndrome"), shaken baby syndrome, spinal cord injuries (including injuries attributable to stretching, bruising, applying pressure, severing, and laceration), peripheral neuropathy disease or trauma, Friedreich's ataxia, Charcot-Marie-Tooth syndrome, diabetic neuropathy, diabetes mellitus, chronic renal failure, porphyria, amyloidosis, liver failure, hypothyroidism, exposure to certain drugs/toxins (including, for example, vincristine, phenyloin, nitrofurantoin, isoniazid, ethyl alcohol, and/or chemotherapeutic agents, organic metals, heavy metals, fluoroquinolone drugs), excess intake of vitamin B6 (pyridoxine), Guillain-Barré syndrome, systemic lupus erythematosis, leprosy, Sjögren's syndrome, Lyme Disease, sarcoidosis, polyglutamine (so called polyQ) diseases, Kennedy disease, Spinocerebellar ataxia Types 1, 2, 3, 6, 7, and/or 17, non-polyglutamine diseases, vitamin (e.g., vitamin B12 (cyanocobalamin), vitamin A, vitamin E, vitamin B1 (thiamin)) deficiency, exposure to physical trauma (e.g., exposure to compression, pinching, cutting, projectile injuries (i.e. gunshot wound), shingles, malignant disease, HIV, radiation, and chemotherapy.

The disclosure includes treating subjects with or at risk of diabetic neuropathy with the compositions disclosed herein to target and thereby modulate (e.g., inhibit) SARM (e.g., SARM1) to reduce axonal and/or synaptic degradation in the subject. Diabetic neuropathies are a family of nerve disorders caused by diabetes. About 60 to 70 percent of people with diabetes have some form of neuropathy. The incidence of neuropathy correlates with duration of disease. The highest rates of neuropathy are among people who have had diabetes for at least 25 years. Diabetic neuropathies also appear to be more common in people who have problems controlling their blood glucose, also called blood sugar, as well as those with high levels of blood fat and blood pressure and those who are overweight. Symptoms of diabetic neuropathy can include pain, tingling, or numbness—loss of feeling—in the hands, arms, feet, and legs. Nerve problems can occur in every organ system, including the digestive tract, heart, and sex organs.

The disclosure includes treating subjects scheduled to undergo and/or undergoing chemotherapy with the compositions disclosed herein to target and thereby modulate (e.g., inhibit) SARM (e.g., SARM1) to reduce axonal and/or synaptic degradation in the subject.

Subject Selection

The present disclosure includes selecting a subject for treatment, e.g., a subject with or at risk of a neurological disorder that manifests and/or includes axonal and/or synaptic degradation (e.g., Wallerian degeneration), e.g., a disorder selected from the exemplary list provided above, and administering to the selected subject an effective amount of a composition disclosed herein.

The term "subject" is used throughout the specification to describe an animal, human or non-human, to whom treatment according to the methods of the present invention is provided. Veterinary and non-veterinary applications are contemplated. Subject selection can include diagnosis and/or referral by a physician or other qualified medical profession and self-referral by the subject to be treated. In some instances, methods can include selecting a subject with one or more of the classes of disease disclosed above. Alternatively or in addition, methods can include selecting a subject with one or more of the diseases disclosed above, or selecting a subject that has been exposed to a medical event, an environmental condition or factor, and/or a toxin known to be associated with an increased risk of or development of neurodegenerative disease. For example, in some instances, methods can include selecting a subject at risk of diabetic neuropathy (e.g., a subject with diabetes mellitus) or a subject with diabetic neuropathy. Methods can also include selecting a subject scheduled to undergo and/or undergoing chemotherapy or treatment with a toxin associated with neurodegeneration.

In some embodiments, the subject is in an early stage of disease, e.g., does not have advanced disease associated with complete neuronal death.

In some embodiments, the compositions and methods described herein do not include treatment of a subject with neurodegenerative disease attributable to oxygen and/or glucose deprivation (e.g., stroke) or Parkinson's disease. For example, selecting a subject can include, where appropriate, excluding subjects with neurodegenerative disease attributable to oxygen and/or glucose deprivation (e.g., stroke) or Parkinson's disease. For instance, selecting a subject can include selecting a subject with a neurodegenerative disease and excluding the selected subject if their neurodegenerative disease is associated with stroke or Parkinson's disease.

Treatment

Treatment can include administration of an effective amount of one or more of the compositions disclosed herein to target and thereby modulate (e.g., inhibit) SARM in a neuron (including in the neuronal cell body), in an axon, in a synapse, and/or in a dendrite. Compositions can be administered by any means that results in inhibition of SARM in a neuron (including in the neuronal cell body), in an axon, in a synapse, and/or in a dendrite. For example, compositions can be administered systemically and/or locally. Systemic administration can include use of compositions that target neurons in the CNS and/or PNS. Local administration can include administration of compositions to a defined region of the CNS and/or PNS, including, but not limited to, an injury site.

Frequency of administration can include once, twice, or more daily administration, for one or more days, and/or for a time that results in treatment of the subject's disease. In some instances, treatment can commence in a subject without neurodegenerative disease or that is at risk for neurodegenerative disease (e.g., in a subject with diabetes but without diabetic neuropathy, and/or in a subject scheduled to be exposed to an agent associated with the onset and/or development of neurodegeneration (e.g., chemotherapy), and/or in a subject that has experienced trauma of the CNS and/or PNS but that does not present symptoms of neurodegenerative disease (e.g., a subject with a head or PNS injury)). Alternatively or in addition, treatment can commence in a subject with neurodegenerative disease. Treatment can include treating a subject without neurodegenerative disease or at risk for neurodegenerative disease, continuing to treat the subject following the onset of neurodegenerative disease, and/or treating a subject that previously had neurodegenerative disease.

Screening Methods

Also included are methods for selecting or identifying compositions, compounds, or agents that modulate (e.g., inhibit) SARM expression and/or activity, for use in the treatment of a neurological disorder that manifests and/or includes axonal and/or synaptic degradation (e.g., Wallerian degeneration), e.g., a disorder selected from the exemplary list provided above. Exemplary compositions can include compositions that interact (e.g., specifically interact) with SARM DNA, mRNA, and/or protein to thereby modulate (e.g., inhibit) SARM mRNA and/or protein expression and/or function. Methods include, for example, screening for candidate compounds using one or more of: in silico, in vitro and/or in culture (e.g., using high-throughput screening methods); and/or animal models (e.g., to test/verify candidate compounds as compounds that inhibit SARM). Compounds can also be evaluated in clinical trial, e.g., for use in human subjects. Techniques for performing such screening methods are known in the art and/or are described herein.

Compounds screened can include, but are not limited to, small molecules, inhibitory nucleic acids, antibodies, and inhibitory peptides. For example, commercial libraries of compounds (e.g., small molecules) can be screened using in vitro high-throughput screening methods. Such libraries include libraries containing compounds (e.g., small molecules) previously approved for use in human subjects (e.g., approved by the Federal Drug Administration).

In silico methods can be used to model the structure of SARM and to predict, model, select, and/or design compounds that interact with SARM or SARM domains (e.g., the SARM α helical domain, the SAM domain, and/or the TIR domain). In vitro methods can include biomolecular (e.g., protein) interaction methods (e.g., using BIARCORE), Fluorescence resonance energy transfer (FRET) in which a SARM binding molecule is used, and/or cellular or genetic reporter assays (e.g., luciferase or fluorescent protein based reporter assays).

Interaction methods can be used to assess the interaction of SARM with a compound or a candidate compound directly or indirectly via competition assay (e.g., wherein a compound or candidate compound competes with a SARM binding partner for SARM binding. In such assays, a decrease in binding of the SARM binding partner to SARM indicates that the compound or the candidate compound interacts with SARM). Such assays can be done in vitro or in cultured cells.

Genetic reporter assays are generally performed in cultured cells. Such assays can be used to screen for compounds that interfere with SARM expression and/or activity directly (e.g., by interaction with SARM) or indirectly (e.g., by interaction with SARM signaling). Useful genetic reporters can include, e.g., SARM (e.g., genetic reporters that include the SARM promoter or a portion thereof operably linked to a genetic reporter protein) and genes that are modulated by SARM (e.g., genetic reporters that include a promoter or portion thereof of a gene that is transcriptionally modulated by SARM). Suitable genes can be up-regulated or down-regulated by SARM. Compounds useful herein can reduce the activity of a gene that is up-regulated by SARM in the absence of the compound. Cell culture methods can also include contacting a neuron with a candidate compound, injuring the neuron by axotomy, and assessing axonal and/or synaptic degradation in the neuron post axotomy. Compounds useful herein can reduce axonal and/or synaptic degradation in the neuron post axotomy.

Animal models can be used to assess candidate compounds, e.g., following their identification in silico and/or in vitro. For example, candidate compounds can be administered to an animal that has neurodegenerative disease to determine whether the candidate compound decreases one or more of: axonal and/or synaptic degradation; and/or reduce one or more symptoms of the disease; and/or reduces disease in the animal model, e.g., relative to disease in the animal in the absence of the candidate compound. Candidate compounds that reduce axonal and/or synaptic degradation; reduce one or more symptoms of the disease; and/or reduce disease in the animal model disease are compound that can be used herein. Various animal models are suitable for use in the screening methods disclosed here. For example, ALS mice and HD mice (DiFiglia et al, PNAS, 104(43):17204-9, 2007) can be used.

EXAMPLES

The invention is further described in the following examples, which do not limit the scope of the invention described in the claims.

Experimental Methods

Unless otherwise noted, the following methods were used in the Examples set forth below.

Drosophila Stocks, Transgenics, and Injury Protocol

The following Drosophila strains were used in this study: OR22a-Gal4; dMP2-Gal4 (Miguel-Aliaga and Thor, Development 131, 6093 (2004)); pUAST-mCD8::GFP; pUAST-nSynaptobrevin::GFP; 201y-Gal4; FRT2A/FRT82B; GMR-hid; Ubi-GFP::nls; FRT2A, tub-Gal80; ey-flp; usp$^2$ (Tp(3; 1)KA21); Ect4-Gal4 (Drosophila Genetic Resource Center); and the 3(L) Deficiency Kit (all from Bloomington Stock Center unless noted). Mutants listed in Table 1 are all from Bloomington Stock Center or generous gifts from: E. Baehrecke; E. Arama; R. Tanguay; M. Guo; N. Tapon; and K. McCall. Lethal mutants were recombined onto a chromosome harboring a flippase recognition target (FRT) sequence and screened using MARCM clonal analysis with ey-flp. To establish mutant stocks for screening, we used the mutagen ethyl methane sulfonate (EMS) and established 2000 individual third chromosome $F_2$ mutant stocks containing FRT sites on both chromosomal arms (2A and 82B). Antennal injury was induced using a modification of a previously described protocol (MacDonald et al., Neuron 50, 869 (Jun. 15, 2006)). Adult flies were aged for 7 days at 25° C. after ablating the right third antennal segment only. Both antennae were ablated for synaptic preservation studies, as ORNs from each antenna synapse on both glomeruli. Injured flies were aged at 25° C. for the indicated time (7, 30, or 50 days) before dissecting and fixing the brain. Axonal integrity was scored as previously described (MacDonald et al., Neuron 50, 869 (Jun. 15, 2006)); Avery et al., J Cell Biol 184, 501 (Feb. 23, 2009)).

Drosophila Immunohistochemistry

Eye-imaginal discs from third instar larvae were dissected and TUNEL stained using In Situ Cell Death Detection Kit (Roche) as previous described (Klein, Methods Mol Biol 420, 253 (2008)). Embryos expressing dMP2-Gal4, UAS-mCD8::GFP were fixed as previously described (Miguel-Aliaga and Thor, Development 131, 6093 (December, 2004)). 1$^{st}$ instar larvae expressing dMP2-Gal4, UAS-mCD8::GFP were imaged live. Whole brains from either pre-pupae or pupae 18 hrs APF were dissected and staining with anti-FasII as described (Lee and Luo, Trends Neurosci 24, 251 (2001)). Embryos from yw or mutant stocks were fixed and staining with anti-FasII as preciously described. Fas II antibody was used at a 1:10 dilution (Developmental Studies Hybridoma Bank). For dsarm rescue experiments, 22aGal4 was recombined with UAS-dsarm using standard fly techniques, and MARCM clones were generated using a line containing ey-flp, UAS-mCD8::GFP. Tdc-Gal4 neurons were imaged using a live fillet preparation (Ataman et al., Neuron 57, 705 (Mar. 13, 2008)). Secondary antibodies were obtained from Jackson Immunolabs and used at 1:200.

*Drosophila* Confocal Microscopy

Samples were mounted in Vectashield antifade reagent and viewed on a III Everest Spinning disk confocal microscope. The entire antennal lobe was imaged in 0.27 µm steps for each sample for scoring axonal integrity. TUNEL-stained eye-imaginal discs were imaged on a Zeiss LSM5 Pascal confocal microscope.

*Drosophila* In Situs

Standard methods were used for collection, fixation, and immunohistochemistry of *Drosophila* yw animals. dSARM cDNA corresponding to exon 5 in dsarm transcript RD was PCR-cloned into pCRII (Invitrogen). Digoxigenin-labeled RNA probes were generated according to the manufacturer's instructions (Roche). RNA in situ hybridization to embryos was carried out as described previously (Broadus et al., Nature 391, 792 (Feb. 19, 1998)). Third-instar larvae were decapitated in 1×PBS and fixed in 9% formaldehyde in PBS for 45 mins. Larval heads were hybridized in hybridization buffer (50% formamide, 5×SSC, 5×Denhardts, 250 ug/ml yeast tRNA, 500 ug/ml herring sperm DNA, 50 ug/ml heparin, 2.5 mM EDTA, and 0.1% Tween-20). Adult heads were decapitated on $CO_2$ and transferred to plastic embedding molds containing Tissue-Tek OCT. The samples were frozen on dry ice, and 15 µm frozen sections were processed for in situ hybridization as previously described (Vosshall et al., Cell 96, 725 (Mar. 5, 1999)), with digoxigenin-labeled riboprobes and detected with TSA-Plus Fluorescein System (Perkin Elmer). Anti-digoxigenin-POD was diluted 1:500 (Roche).

Antibodies and Reagents for Mammalian Studies

Antibodies used in this study were: mouse monoclonal anti-Tau-1 (clone PC1C6, #MAB3420), and rabbit anti-neurofilament-M (#AB 1987) from Millipore; rabbit monoclonal anti-β-tubulin class III (#MRB-435P), and rabbit anti-α-internexin (#PRB-572C) from Covance; mouse monoclonal anti-β-actin (clone AC-15, #A5441) from Sigma; rat monoclonal anti-CD11b (clone M1/70.15, #MCA74EL) from AbD Serotec; rabbit anti-synaptophysin (#08-0130) from Invitrogen. Monoclonal neutralizing antibody against mouse NGF was previously described (Nikolaev et al., Nature 457, 981 (Feb. 19, 2009)). Secondary detecting antibodies conjugated with indicated Alexa dyes, and Alexa-594 conjugated α-bungarotoxin were from Invitrogen. Goat serum, donkey serum, and horseradish-peroxidase conjugated donkey anti-rabbit IgG and donkey anti-mouse IgG were from Jackson ImmunoResearch. All other chemicals were from Sigma unless otherwise specified.

Mouse Surgery and Immunohistochemistry

All surgical and experimental procedures in mice were performed in compliance with the protocols approved by the Institutional Animal Care and Use Committee of The Rockefeller University, Cornell Weill Medical College, and The University of Massachusetts Medical School. Mice were anesthetized with isoflurane, and the skin on their right hind limb was shaved and prepared with iodine and alcohol. An incision was made between the knee and the hip joint, and the gluteal muscles were separated carefully with a pair of forceps. The sciatic nerve was transected as close to the thigh with a pair of sterile surgical scissors, and 1- to 2-mm of nerve segment was removed to prevent the regeneration of axons into the distal stump. The gluteal muscles were then brought back into their original anatomical position, and the overlying skin was re-approximated by surgical staples or sutures.

For light microscopy, the animals were euthanized at indicated time points post-surgery and nerve segments 3-6 mm distal to the lesion fixed with 4% paraformaldehyde and 2.5% glutaraldehyde in 0.1 M PBS, pH 7.4 (72 h at 4° C.). After an extensive wash in 0.1 M PBS, 2 h of postfixation (1% osmium tetroxide) and dehydration in graded ethanol and propylene oxide, nerve segments were embedded in Durcupan resin (Fluka Chemie). After polymerization for 48 h at 60° C., transverse semithin sections (0.5 µm) were cut on a Leica ultramicrotome, stained with toluidine blue and photomicrographed. To quantify survival, 500 randomly chosen axons were counted. Survival criteria were normal myelin sheaths, uniform axoplasm and intact, unswollen mitochondria. A two-tailed one sample t-test was performed using GraphPad Prism 5.

For the biochemical analysis of sciatic nerves, the animals were euthanized at indicated time points post-surgery. A 10-mm segment of the nerve distal to the transection site was harvested, and immediately homogenized in 200 ul Urea/SDS buffer [50 mM Tris-Cl (pH 6.8), 8.0 M urea, 10% (w/v) SDS, 10 mM sodium EDTA, and 50 mM DTT]. The nerve samples from two Sarm1+/+ or Sarm1−/− mice were processed for each time point. After heating at 95° C. for 10 min, 10-ul aliquot of each nerve homogenate was subjected to 4-15% gradient Tris-glycine SDS-PAGE (Bio-Rad), and transferred to Immobilon-P PVDF membranes (Millipore) for immunoblot analysis. The membranes were immunoblotted with the indicated primary antibodies, and then the corresponding secondary antibodies in PBS/Tween-20. The bound antibodies were visualized by SuperSignal chemiluminescence reagents (Pierce). All membranes were exposed to Phoenix Blue X-ray film for 5 to 10 sec.

For immunohistochemistry, the mice were lethally anesthetized at the indicated time points post-surgery, and transcardially perfused with 4% paraformaldehyde/PBS. The sciatic nerves distal to the transection site was dissected, and post-fixed in 4% paraformaldehyde/PBS at 4° C. overnight. After washing three times in PBS, the nerves were cryoprotected in 30% (w/v) sucrose/PBS at 4° C. overnight, and then frozen in the 2:1 mixture of 30% sucrose/PBS:OCT (Tissue Tek) for 12-um longitudinal cryosections. The nerves were permeabilized in 0.5% Triton X-100/PBS for 1 hour, and blocked in 0.5% Triton X-100/PBS containing 2% bovine serum albumin, and 4% goat serum at 4° C. overnight. Immunohistochemistry was carried out with either rabbit anti-neurofilament-M (1:500) or rat anti-CD11b (1:500) in the same blocking buffer at 4° C. overnight, followed by washing for 1 hour in 0.5% Triton X-100/PBS three times. The sections were then labeled with the corresponding Alexa-488 or Alexa-568 conjugated secondary antibodies for 2 hours, washed in PBS, and mounted in fluoromount-G. Images were taken at 2-mm distal to the transection sites, and 3 nonadjacent sections of each nerve sample were examined. Four (neurofilament-M axons) or three (CD11b macrophages/monocytes) mice of Sarm1+/+ or Sarm1−/− were included per time point.

To examine denervation at neuromuscular junctions, the tibialis anterior muscles were dissected from perfused animals, and post-fixed in 1% paraformaldehyde/PBS at 4° C. overnight. After washing three times in PBS, muscles were cryoprotected in 30% sucrose/PBS at 4° C. overnight, and embedded in OCT for 80-um longitudinal cryosections. The tissues were permeabilized in 0.5% Triton X-100/PBS for 1 hour, and blocked in 1% Triton X-100/PBS containing 4% bovine serum albumin, and 4% donkey serum at 4° C. overnight. To label axons and neuromuscular junctions, muscles were stained with rabbit anti-neurofilament-M (1:500) and rabbit anti-synaptophysin (1:5) in the same blocking buffer at 4° C. for at least 24 hours. After washing for 1 hour in 0.5% Triton X-100/PBS three times, the muscles were incubated with Alexa-647 conjugated donkey anti-rabbit antibody (1:500) and Alexa-594 conjugated a-bungarotoxin (1:1000) overnight. After washing in PBS for 4 hours, sections were mounted in fluoromount-G, and imaged by LSM 510 laser scanning confocal microscope. To analyze presynaptic structures, maximum-intensity projections of z-stack images from 6 to 8 nonadjacent sections of each muscle sample were generated by AutoQuant X. Partial or full denervation was determined as the postsynaptic AChR sites not apposed by the presynaptic marker (colored in green for better visualization). About 100 neuromuscular junctions were examined for each muscle, and four Sarm1+/+ or Sarm1−/− mice were included per time point.

Example 1

Identification of Genes Involved in Axonal Degradation

The *Drosophila* olfactory system is a model system for Wallerian degeneration. To determine whether Wallerian degeneration might be related to previously described cell destruction programs, a comprehensive screen of existing mutants and dominant negative constructs was performed for *Drosophila* genes affecting apoptosis, autophagy, or other defined cell degradative pathways, but these failed to suppress Wallerian degeneration in vivo at any level (Table 1).

TABLE 1

Mutations of known cell death and degeneration genes in *Drosophila* that do not block Wallerian degeneration

| Gene | Mutant Allele | Allele Type |
|---|---|---|
| ask1/pk92B | DN | OE |
| atg1 | Δ3D | LOF |
| atg1 | KQ #5B | OE of DN |
| atg1 | 68 | OE of DN |
| atg1 | EP3009 | LOF |
| atg1 | KG03098 | LOF |
| atg1 | EP3348 | LOF |
| atg2 | EP3697 | LOF |
| atg6 | 0.00096 | LOF |
| atg7 | d77 | LOF |
| atg7 | d14 | LOF |
| atg18 | KG03098 | LOF |
| bsk/Jnk | DN | OE |
| bsk/Jnk | flp147E | LOF |
| buffy | H37 | LOF |
| calcineurin A1 | ED6346 | DEF |
| calcineurin A1 | BSC749 | DEF |
| calx | UAS | OE |
| CaMKII | UAS | OE of DN |
| cullin-3 | mds1 | LOF |
| cullin-3 | UAS | OE |
| cyt-c d | bin1 | LOF |
| damm | f02209 | LOF |
| dark | CD4 | hypomorph |
| dark | CD8 | hypomorph |
| debcl | E36 | LOF |

TABLE 1-continued

Mutations of known cell death and degeneration genes in *Drosophila* that do not block Wallerian degeneration

| Gene | Mutant Allele | Allele Type |
|---|---|---|
| debcl | W105 | truncated 5' |
| dIAP/thread | th1 | LOF |
| dIAP/thread | UAS | OE |
| dIAP2 | G2326 | OE |
| dredd | B118 | Null |
| dronc | CG | OE of DN |
| dronc | 51 | LOF |
| drp1 | KG03815 | LOF |
| dunce | 1 | Null |
| hsp22 | EP(3)3247 | OE |
| ik2 | KAIA | OE of DN |
| imd | 1 | Null |
| mstprox/toll-3 | Exel 6146 | Def |
| omi/htra2 | UAS | OE |
| omi/htra2 | Δ07 | LOF |
| p35 | UAS | OE |
| pmn | UAS | OE |
| puckered | UAS | OE |
| roc1b | dc3 | LOF |
| sod1 | UAS | OE |
| strica | 4 | Null |
| toll-6 | ex13 | Null |
| toll-7 | g1.1 | Null |
| tollo | 59 | Null |
| tor | TED | UAS of DN |

All mutants or misexpression constructs were crossed into a background where a subset of ORNs were labeled with GFP (22a-Gal4, UAS-mCD8::GFP). ORN axons were severed, and degeneration was scored 5 days after axotomy. LOF = reported amorphic loss of function allele; OE = overexpression construct (under UAS- promoter control); DN = dominant negative; FL = full length of unmutagenized gene. n ≥ 10 antennal lobes for all.

To identify new genes required to promote axon auto-destruction an $F_2$ forward genetic screen was performed in *Drosophila* for mutants that exhibited survival of axons after axotomy (FIG. 5). Because genes required for Wallerian degeneration may cause lethality when mutated, the screen was designed to allow for the isolation of essential and non-essential genes by characterization of both viable and lethal mutants though MARCM clonal analysis (Lee and Luo, Trends Neurosci 24, 251-254 (2001)).

A third chromosome line harboring flipase recombination target (FRT) sites, FRT2A, FRT82B, at the base of both arms of chromosome 3 was used. Methods started with a third chromosome isogenized strain where a subset of olfactory receptor neuron (ORN) axons were labeled with membrane tethered GFP (OR22a-Gal4, UAS-mCD8-GFP), mutagenized with EMS, and established ~2500 individual mutant $F_2$ stocks. If mutant lines were homozygous viable for the third chromosome, unilateral axotomy was induced in homozygotes by ablating the right antenna and assayed. Axonal integrity was assessed one week later via unilateral ablation of antennae. If mutant lines contained lethal mutations on chromosome 3, MARCM clones (Lee and Luo, Trends Neurosci 24, 251-254 (2001)) were generated in ORNs individually for 3R and 3L. Axotomies were performed and analyzed as described for the viable lines.

Axotomy in wild type flies resulted in severed axons being completely cleared from the right antennal lobe within 1 week after injury (FIG. 1A-wild type). In contrast, certain mutants showed normal axon function post-axotomy. Specifically, four lethal lines, l(3)896, l(3)4621, l(3)4705, and l(3)7152, were identified in which severed axons generated by MARCM remained intact 1 week after axotomy (FIG. 1A). While the number of uninjured axons was slightly reduced in each mutant, 100% of GFP-labeled axons exhibited long-term preservation after injury (Table 2, below). Remarkably, mutant axons remained fully intact 30 days after injury (FIG. 1B) and a significant but reduced number remained morphologically intact even 50 days after injury (FIG. 1C). l(3)896, l(3)4621, and l(3)4705 therefore provide axonal preservation that rivals that of Wlds in *Drosophila*, and which lasts essentially for the lifespan of the fly. As described in more detail below, intact axons were also observed 30 days and 50 days post axotomy (FIGS. 1B and 1C). Neuroprotection in these mutants extended to synapses: synaptobrevin punctae localized to synaptic terminals even 30 days after axotomy (see below and FIGS. 1D and 1E). In each of these mutants OR22a+ axonal morphology, pathfinding, and innervation of antennal lobe glomeruli appeared normal, suggesting that none of these mutants grossly affected ORN development. All four mutants were homozygous lethal, and failed to complement one another for lethality. Thus each appears to represent an independently isolated lethal mutation in the same gene.

Figure 1F:
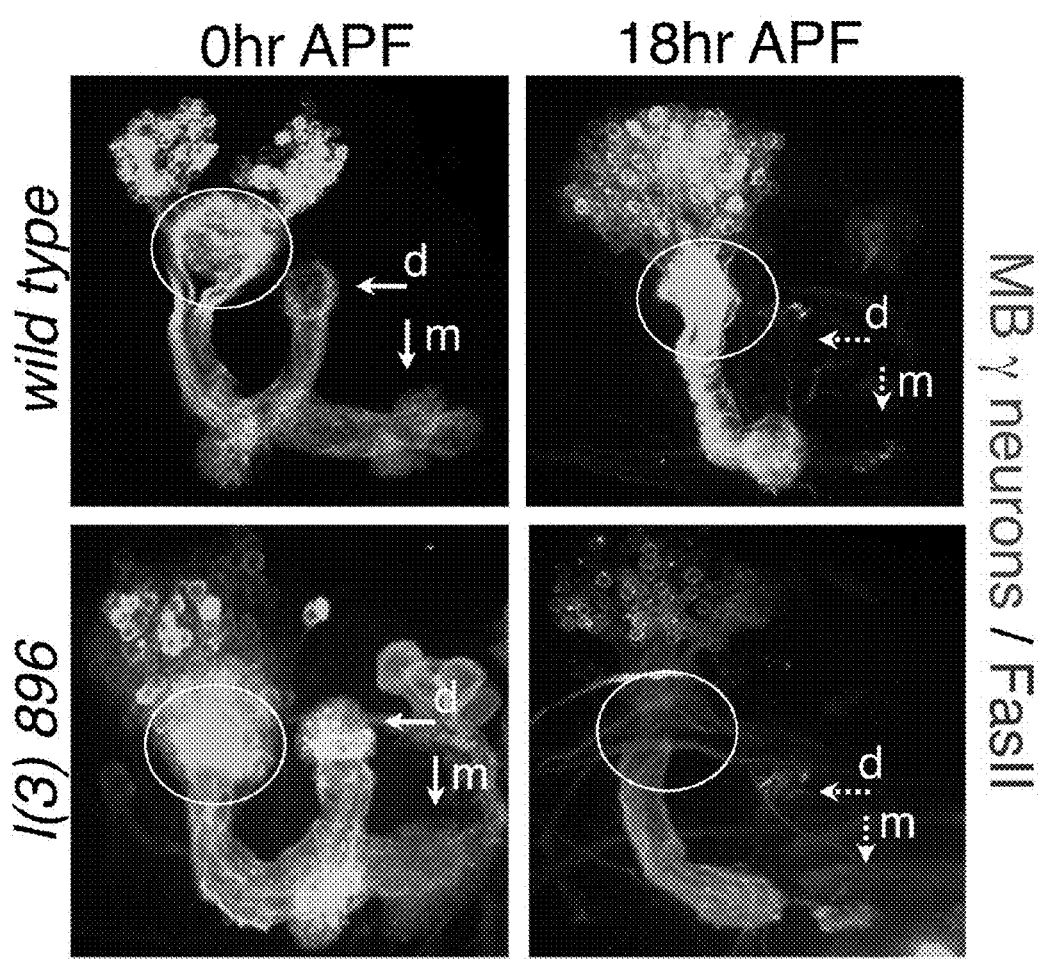
Figure 1G:
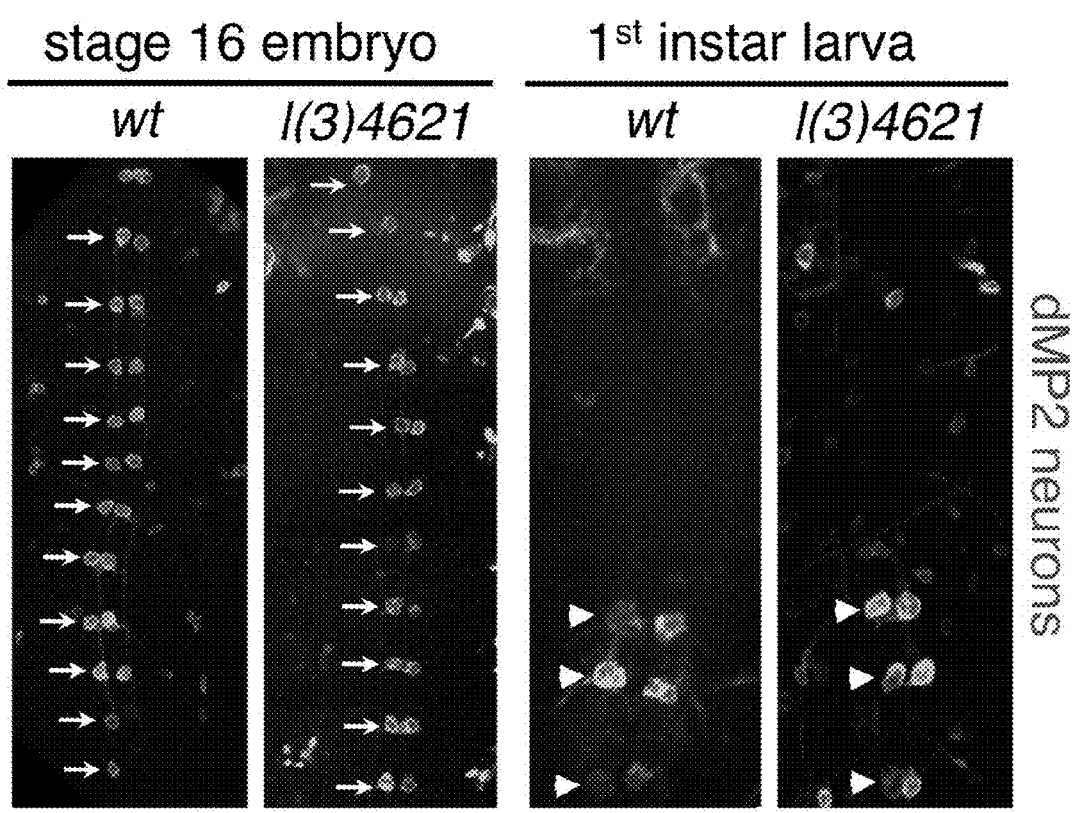
Figure 1H:
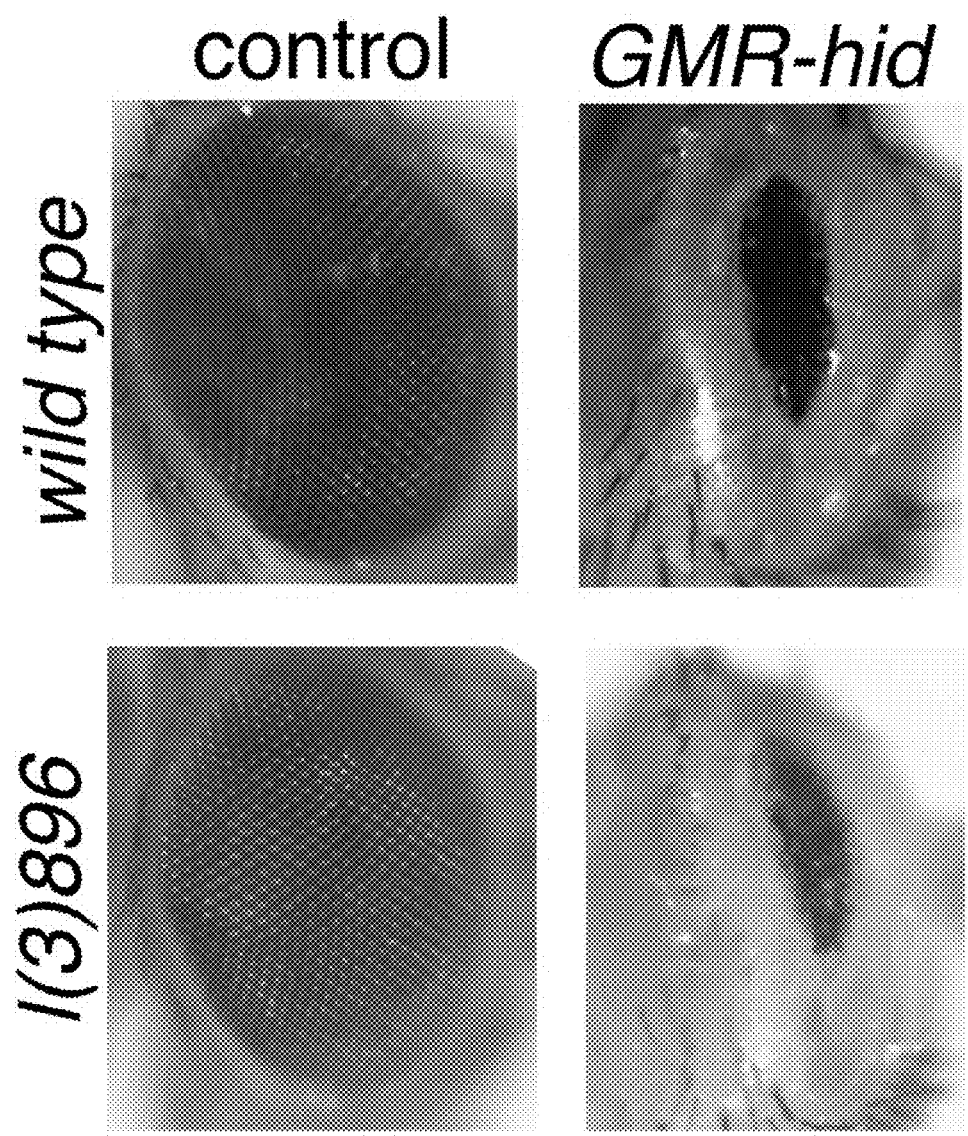
Figure 1I:
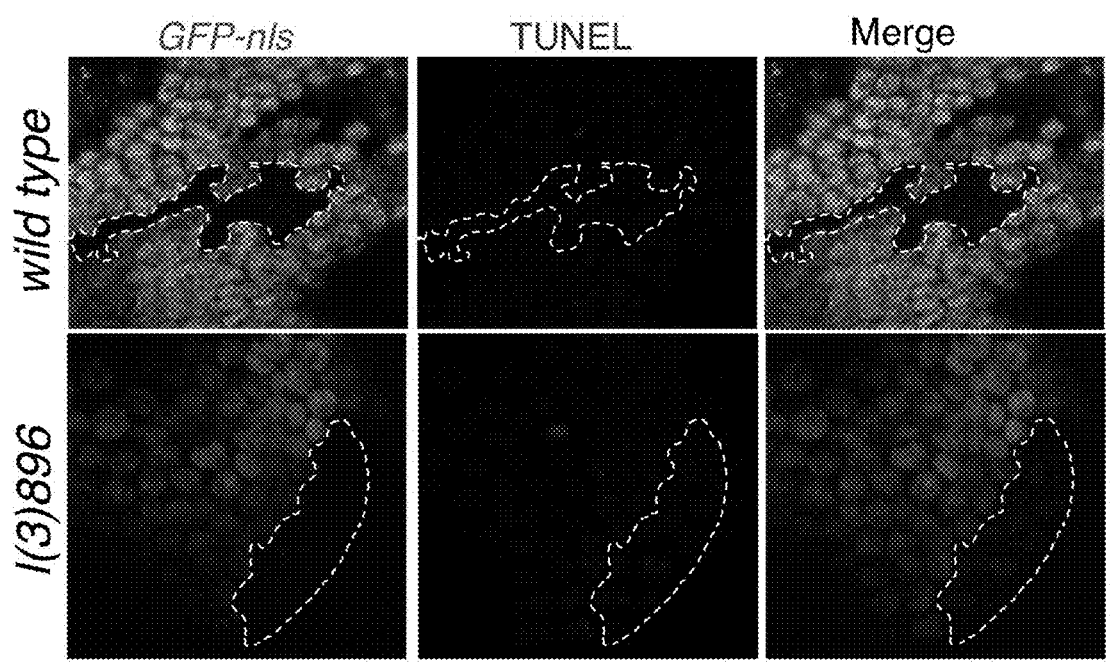

Previous work (9, 10, 12) and the present data argue that Wallerian degeneration is molecularly distinct from apoptosis and developmental neurite pruning. To determine whether l(3)896 is broadly required for neuron pruning or apoptotic cell death, MARCM clones were examined in *Drosophila* mushroom body γ neurons, as these neurons undergo both dendritic and axonal pruning during metamorphosis (15). In both control and l(3)896 animals, mushroom body γ neuron axons and dendrites were pruned normally (FIG. 1F). During normal early embryogenesis, dMP2 neurons are present in each segment, but by late embryogenesis, all but the posterior 3 pairs undergo developmentally-programmed apoptosis (16). dMP2 neurons were generated normally in l(3)4621 animals, and the appropriate subset of neurons underwent apoptosis (FIG. 1G). Finally, the pro-apoptotic gene hid was expressed in the *Drosophila* visual system (17) to induce widespread apoptotic death in cells of the developing eye disc. The l(3)896 mutant clones failed to suppress activation of cell death (FIGS. 1H and 1I).

Example 2

Validation of Axonal Protection for MARCM Clones

To determine the penetrance of axonal protection, MARCM clones were generated in the indicated mutant strains. Axons labeled with OR22aGal4, UAS-mCD8::GFP were aged for 7 days after eclosion, followed by unilateral antennal ablation. Axonal integrity was scored 7 days after injury in both uninjured and injured glomeruli. n≥10 lobes for all. Data is presented in Table 2.

TABLE 2

Production of MARCM clones and persistence of severed axons in axon protective mutant backgrounds

| Mosaic chromosome | Number of Axons (uninjured)* | Number of Axons 7 days post axotomy* |
|---|---|---|
| Wild type | 11.08 +/− 1.52 | 0 |
| l(3)896 | 4.71 +/− 1.76 | 5.43 +/− 2.12 |
| l(3)4621 | 7.44 +/− 0.66 | 6.13 +/− 0.74 |
| l(3)4705 | 4.94 +/− 0.85 | 5.00 +/− 1.61 |

*Number of individual axon fibers identified in z-stacks from confocal imaging of entire antennal lobe. N => 10.

As shown in Table 2, on average, control chromosomes led to the production of 11.08±1.52 GFP-labeled axons in MARCM clones. In contrast, in l(3)896, l(3)4621, and l(3)4705 backgrounds, 4.71±1.76, 7.44±0.66 and 4.94±0.85 GFP-labeled axons in MARCM clones were observed. The observed consistently reduced number of axons labeled in mutant background indicates that loss of the affected gene's function results in a growth disadvantage for ORNs compared to wild type cells (see the column entitled "uninjured"). However, the number of GFP-labeled axons that exhibit long term survival in each of the mutants is not significantly different from the number labeled prior to injury, indicating in each of these mutant backgrounds essentially 100% of axons were protected 1 week after injury.

Example 3

Duration of Axonal Protection

In *Drosophila* Wld$^S$ expression is sufficient to protect severed axons for 30-40 days after axotomy, but beyond that time point axons degenerate (Avery et al., J. Cell. Biol., 184:501-513, 2009). Axonal integrity was assessed in the mutants described above at 30 and 50 days post axotomy. As shown in FIGS. 1B-1C, in l(3)896, l(3)4705, l(3)4621, and l(3)7152 mutant clones axons remained fully intact 30 and 50 days post axotomy. Since Wld$^S$-mediated axon protection disappears by day 50, these mutants exhibit axon protective phenotypes that significantly exceed Wld$^S$. Moreover, the median lifespan of *Drosophila* is ~30 days, thus severed axons are protected in these mutants for essentially the entire lifespan of the fly.

Example 4

Characterization of MARCM Clones—Identification of dSARM

Figure 2A:
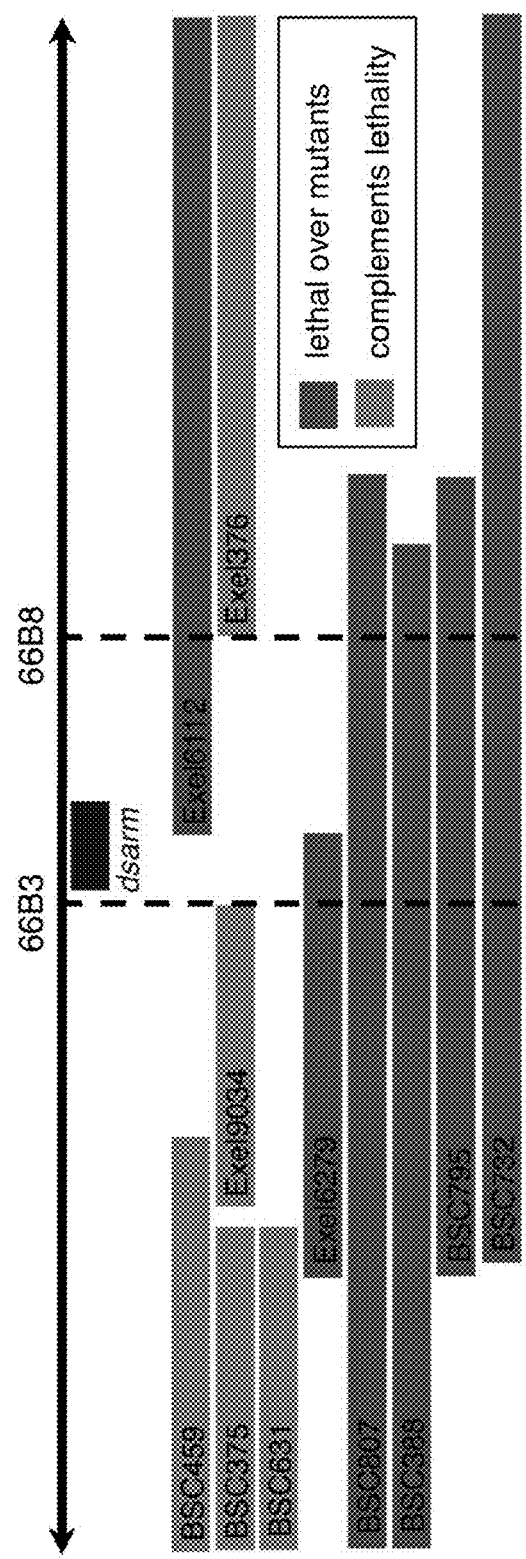

Two approaches were employed to identify the gene affected in l(3)896, l(2)4621, l(3)4705, and l(3)7152 mutants. First, lethality was mapped using small chromosomal deficiencies. By assaying for non-complementation it was possible to map the lethality to a single gene, Ect4 (hereafter referred to as dSARM for *Drosophila* SARM), using an array of partially overlapping deficiencies in the 66B region of chromosome 3 (FIG. 2A).

In addition, next-generation sequencing technology was used to re-sequence the entire genome of each mutant (along with the unmutagenized control line) to an average read depth of 70× in order to identify novel mutations in open reading frames in genes on 3L, and more specifically, any gene mutated in all four mutant backgrounds (Table 3).

TABLE 3

Identification of dsarm through re-sequencing of mutant genomes

| | One mutant line (# of genes) | Any two mutant lines (maximum # of genes) | All three mutant lines (# of genes) |
|---|---|---|---|
| Unique coding variants; genome wide | 92 (l(3)896)<br>997 (l(3)46210)<br>272 (l(3)4705) | 166 | 6 |
| Unique coding variants; chromosome 3L | 34 (l(3)896)<br>132 (l(3)46210)<br>46 (l(3)4705) | 8 | 3 |
| + nonsynonymous or splice site and heterozygous changes | 17 (l(3)896)<br>66 (l(3)46210)<br>23 (l(3)4705) | 2 | 1 |

The number of identified variants are indicated within and across mutant lines. Filtering strategy was as indicated above.

This approach identified a single gene affected in all of the mutants which resided in cytogenetic region 66B: ect4, which is referred to herein as dsarm (*Drosophila* sterile alpha and Armadillo motif). The dsarm gene encodes a protein with an Armadillo/HEAT (ARM) domain, two sterile alpha motifs (SAM), and a Toll/Interleukin-1 Receptor homology (TIR) domain. Each identified dsarm allele contained a unique premature stop codon in dsarm open reading frame (FIGS. 2B, 2C).

Figures 2B, 2C:
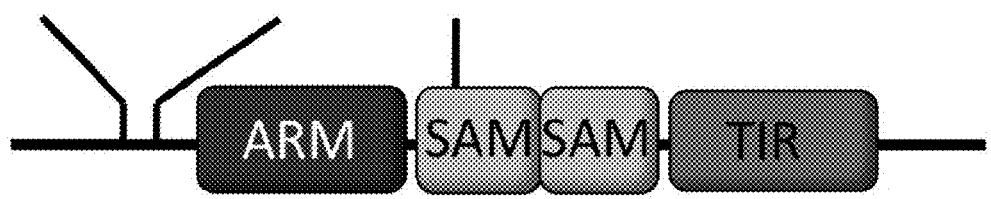

As illustrated in FIG. 2C, the l(3)896, l(2)4621, and l(3)4705 mutants each contained a unique premature stop codon in dSARM. The predicted protein products from l(3)896 and l(2)4705 would be truncated prior to the ARM, SAM, and TIR domains; that from l(2)4621 would be truncated early in the first SAM domain. l(3)7152 is a point mutation in the first SAM domain (1986S). These observations confirm that the MARCM mutations are recessive and that three of the four alleles result in premature stop codons. Accordingly, the mutations are loss-of-function mutations.

To test this interpretation, dsarm was cloned for expression studies. The first 630-4828 nucleotides of the partial dsarm cDNA GH07037 (DGRC) was cloned into the pCashsp40-LacZ vector with BglII/XhoI. The remaining sequence was obtained by PCR amplifying a fragment from cDNA IP03452 (DGRC) using 5'ECT4-D NotI (atatatgcg-gccgcaaaacATGGGCAATCGTTTGAGCGGC; SEQ ID NO:7) and PM001 (CGTTAGAACGCGGCTACAAT; SEQ ID NO:8), then cut with NotI/BglII and ligated into the pCashsp40-LacZ vector. The resulting full length dsarm was then PCR amplified off the pCashsp40-LacZ vector using the above 5'ECT4-D NotI and 3' Ect4-D aa1610-1637 (aga-tactcgagTTACCAAAATATCATGCGCCCGGCAT-TGGGGGAGGTGGCCTTGGA CAGAATGATGC-CCGAAAGTTCCTCGTCCTCCATTTCGTTGTTTTTTA TCAGCG AGCGGACCTTCTTCATCG; SEQ ID NO:9), cut with NotI/XhoI, and ligated into pUAST vector (generating pUASt-dsarm). pUASt-dSarm::GFP was generated by cloning into the NotI/SpeI sites of pUASt-CT EGFP with PCR-amplification off the pUASt-dsarm construct using 5'ECT4-D NotI and 3' ECT4-D SpeI (gatcactagtC-CAAAATATCATGCGCCCGGCATTGG; SEQ ID NO:10).

Figure 2D:
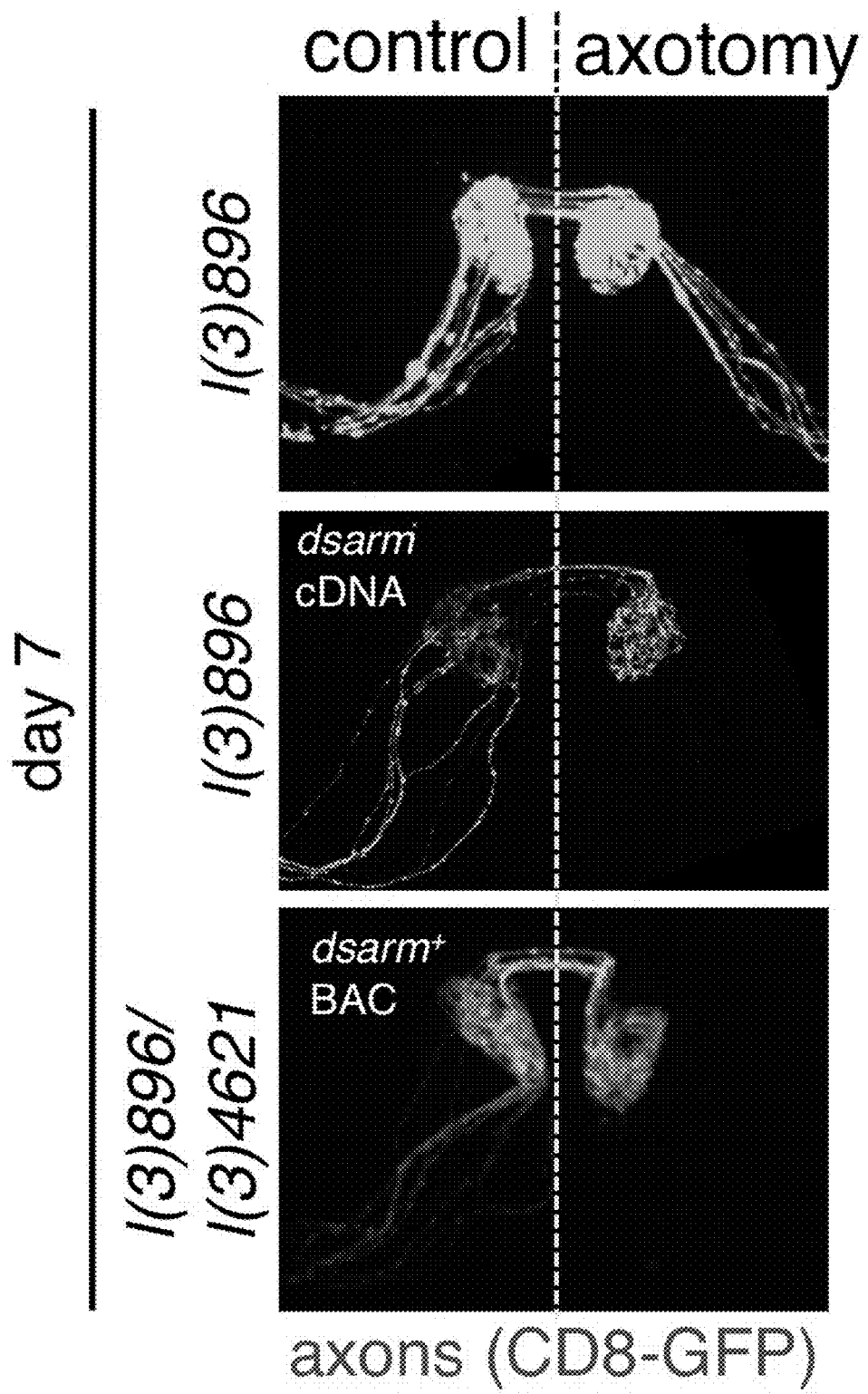

The results were consistent with the above interpretation; expression of full length dsarm cDNA using the postmitotic OR22a-Gal4 driver in l(3)896 mutant clones was sufficient to fully revert the suppression of axonal degeneration observed in dsarm mutants (FIG. 2D). In addition, both the lethality and suppression of Wallerian degeneration phenotypes were rescued in l(3)896/l(3)4621 and l(3)896/Df(3L) BSC795 trans-heterozygous animals with a BAC clone containing the dsarm gene. Together these data indicate that dsarm is necessary in post-mitotic neurons for axonal destruction after axotomy, and loss of dsarm function is sufficient to provide long-term preservation of severed axons.

Based on RNA in situ hyridizations to embryos, larval brains, and adult brains, RT-PCR from dissected neural tissues, and analysis of a dsarm-Gal4 driver line, dsarm appears to be widely expressed in the *Drosophila* nervous system. This observation suggests that dSarm is broadly required to promote Wallerian degeneration in the nervous system.

Example 5

Functional Characterization of dSARM

A number of cell degradative programs are engaged to dispose of neurons, or parts of neurons including apoptotic cell death pathways and axonal pruning or dendritic pruning programs (Raff et al., Science, 262:695-700, 1993; Luo and O'Leary, Annu Rev. Neurosci., 28:127-156, 2005). $Wld^S$ does not block cell death or developmental axon pruning and, reciprocally, molecules that block apoptotic cell death do not block axon degeneration after injury (Simonin et al, Eur. J. Neurosci., 25:2269-2274, 2007; Hoopfer et al., Neuron, 50:883-895, 2006; Finn et al., J. Neurosci., 20:1333-1341, 2000).

To determine whether dSARM mutations were capable of affecting other types of neuronal degradation besides Wallerian degeneration, MARCM clones were generated in *Drosophila* mushroom body γ neurons using control and $dSARM^{896}$ chromosomes.

MARCM clones were generated with wild type or $dSARM^{896}$ chromosomes during larval stages using the 201Y-Gal4 driver, which labels mushroom body γ neurons. Dendretic and axonal pruning in the dorsal and medial bindles were scored at 0 and 18 hours after puparium formation (APF). As shown in FIG. 1F, in both control (wild type) and $dSARM^{896}$ animals, γ neuron axons and dendrites were fully pruned by 18 hours after pupariaum formation. These data indicate that loss of dSARM function does not affect developmental neurite pruning The potential role of dSARM in naturally occurring and induced cell death during development was also examined. First, the dMP2-Gal4 driver was crossed into control and $dSARM^{4621}$ backgrounds. This marker allows for the unique identification of the dMP2 neurons which are initially generated in each embryonic segment, but later undergo cell death in all segments but A7-9 before the 1st instar larval stage (Miguel-Aliaga and Thor, Development, 131:6093-6105, 2004). As shown in FIG. 1G, dMP2 neurons were generated normally in both control and $dSARM^{4621}$ animals and the appropriate subsets underwent cell death prior to larval hatching. Further, the normal complement of dMP2 neurons were identified in stage 16 embryos, and all underwent programmed cell death expect the 3 most posterior abdominal pairs by $1^{st}$ instar larval stages.

To evaluate the role of dSARM in cell death, cell death was induced in the developing visual system using the GMR-hid approach (Grether et al., Genes Dev., 9:1694-1708, 2005), and made clones of both control and $dSARM^{896}$ chromosomes and assayed for any suppression of cell death (e.g. rescue of eye ablation).

As shown in FIG. 1H, it was found that dSARM mutations had no effect on the activation of cell death in the visual system by hid expression.

These data reveal that dSARM has no effect on the activation or execution of neurite pruning or apoptotic cell death.

In addition, our studies revealed axonal degeneration is not impacted by the loss of known autophagic or apoptotic genes, including the autophagy genes PTEN, TOR, Atg 1, 2, 6, 7, and 18; and the apoptosis genes Cyt C Diap1, Diap2, Debcl Buffy, Dronc, Roc2, Gft, Cul3, Dark, and p35.

Example 6

Mammalian SARM1 Mediates Wallerian Degeneration

Wallerian degeneration was next assayed in null mutants for the mouse ortholog of dsarm, Sarm1. Five day cultures of superior cervical ganglia (SCG) were cultured from wild type, Sarm1−/−, and $Wld^s$ mice, severed axons, and axonal integrity scored over the next week. Similar experiments were conducted in dorsal root ganglion (DRG) and cortical neuron cultures.

SCG explants were dissected from 0-2 day old pups and cultured as previously described (Gilley and Coleman, PLoS Biol 8, e1000300 (2010)). Axons were allowed to extend for 5 days before separation from the cell body mass using a scalpel. The degeneration of the isolated axons was followed at different time points for 72 h after cut. Bright field images were acquired on a microscope (IX8I; Olympus) coupled to a digital camera (U-TV 0.5XC; Olympus) using AnalySIS software (Soft Imaging Systems GmbH, Germany). Axonal protection was quantified as described (Gilley and Coleman, PLoS Biol 8, e1000300 (2010)). Typically an image of intact axons has a protection index (PI) value around 1. A PI around 0 occurs when axons detach from the dish. A two-way repeated measures analysis of variance (ANOVA) was used to show the difference in axonal protection between wild-type and Sarm−/−. For dissociated SCG cultures, cells were microinjected as previously described (Gilley and Coleman, PLoS Biol 8, e1000300 (January, 2010)) with 50 ng/µl of mito-tagRFP construct created by PCR amplification of the mitochondrial targeting sequence (aa 1-24) of Mus musculus cytochrome c oxidase subunit VIIIb (GenBank AK003116.1) and insertion into the MCS of the pTagRFP-N vector (Evrogen). 24 hours after microinjection cultures were immunostained using 0.3 µg/ml mouse monoclonal anti-SARMI antibody (Chen et al., J Cell Biol 193, 769 (2011)) and Alexa-488 secondary antibody. Cultures were visualized on an Olympus FV1000 point scanning confocal microscope using a 60×1.35NA apochromat objective.

For cortical neuron cultures, Campenot dividers (Tyler Research) were set up in poly-D-lysine/laminin-coated 2-well chamber culture slides. On DIV 0 (Day In Vitro 0), neocortices were dissected from six E16.5 Sarm1+/+ or Sarm1−/− embryos, pooled, and dissociated in Hank's Balanced Salt Solution (without $Ca^{2+}$ and $Mg^{2+}$, Invitrogen) containing 0.05% (w/v) trypsin/EDTA at 37° C. for 10 min. After adding a final concentration of 10% (v/v) heat-inactivated fetal bovine serum (HI-FBS), the tissues were spun down at 500 g for 3 min. The tissues were then suspended and triturated in Neurobasal/B-27 medium [Neurobasal medium supplemented with 2% (v/v) B-27, 2 mM glutamine, 100 U/ml penicillin, and 100 ug/ml streptomycin] containing 10% HI-FBS. The cells were plated in the cell-body compartment of Campenot dividers at a density of $2.5×10^5$ per well. To facilitate the axotomy later, Campenot dividers were removed after 6 hours, when the cells already attached to the slides. From DIV 3, half of the culture medium was replaced every other day by fresh Neurobasal/B-27 medium containing 5 uM 5'-fluorouridine and 5 uM uridine to suppress the proliferation of non-neuronal cells. On DIV 10, the cultures were subjected to axotomy.

For the dorsal root ganglion (DRG) cultures, DRGs were dissected from four E13.5 Sarm1+/+ or Sarm1−/− embryos on DIV 0. The explants from each embryo were individually plated in poly-D-lysine/laminin-coated 4-well chamber culture slides in F-12/N-3 medium [Ham's F-12 medium supplemented with 40 mM glucose, 4% (v/v) N-3 supplement, and 50 ng/ml mouse NGF]. On DIV 1, the cultures were changed to fresh F-12/N-3 medium containing 1 µM cytosine β-D-arabinofuranoside to suppress the proliferation of non-neuronal cells. On DIV 3, the explants were subjected to either the axotomy, or the NGF deprivation with a final concentration of 50 ug/ml anti-NGF antibody.

To visualize the axons, the cultures were fixed in 4% paraformaldehyde (w/v)/phosphate-buffered saline (PBS) at room temperature for 30 min, followed by the permeabilization with 0.1% (v/v) Triton X-100/PBS for 30 min. The axons were then immunostained with the indicated primary antibodies in 0.1% Triton X-100/PBS containing 2% (w/v) bovine serum albumin, and 2% (v/v) goat serum at 4° C. overnight, followed by the corresponding Alexa-488 or Alexa-568 conjugated secondary antibodies. To quantify axon degeneration, the images of distal axons were taken from 2 random fields per well, and 40 to 80 singly distinguishable axons in each field were examined, with any sign of fragmentation scored as degeneration. For each time point, 4 wells of Sarm1+/+ or Sarm1−/− cortical neuron cultures, or the DRG explants from 4 embryos of Sarm1+/+ or Sarm1−/−, were included.

Sarm1−/− SCG explants exhibited robust protection from degeneration up to 72 hours after axotomy, similar to what is observed with $Wld^S$ SCG neurons, while wild type axons degenerated within 8 hours (FIG. 3A,B). This robust protection was also seen in cultured Sarm1−/− cortical neuron axons (FIG. 3C,D) and dorsal root ganglia (DRG) (FIG. 3E,F). Notably, Sarm1−/− DRG explants were not protected from nerve growth factor (NGF) deprivation (FIG. 3G,H), a mouse model for developmental axon pruning (4, 15, 18, 19), suggesting that in mammals Sarm1 protection is specific to injury-induced axon degeneration. Thus Sarm1 loss of function robustly suppresses Wallerian degeneration in multiple types of mammalian axons in vitro. In addition, based on use of culture conditions that minimize the presence of satellite cells among the axons, the present data argue that Sarm1 is required cell autonomously for programmed axonal death.

Figure 4C:
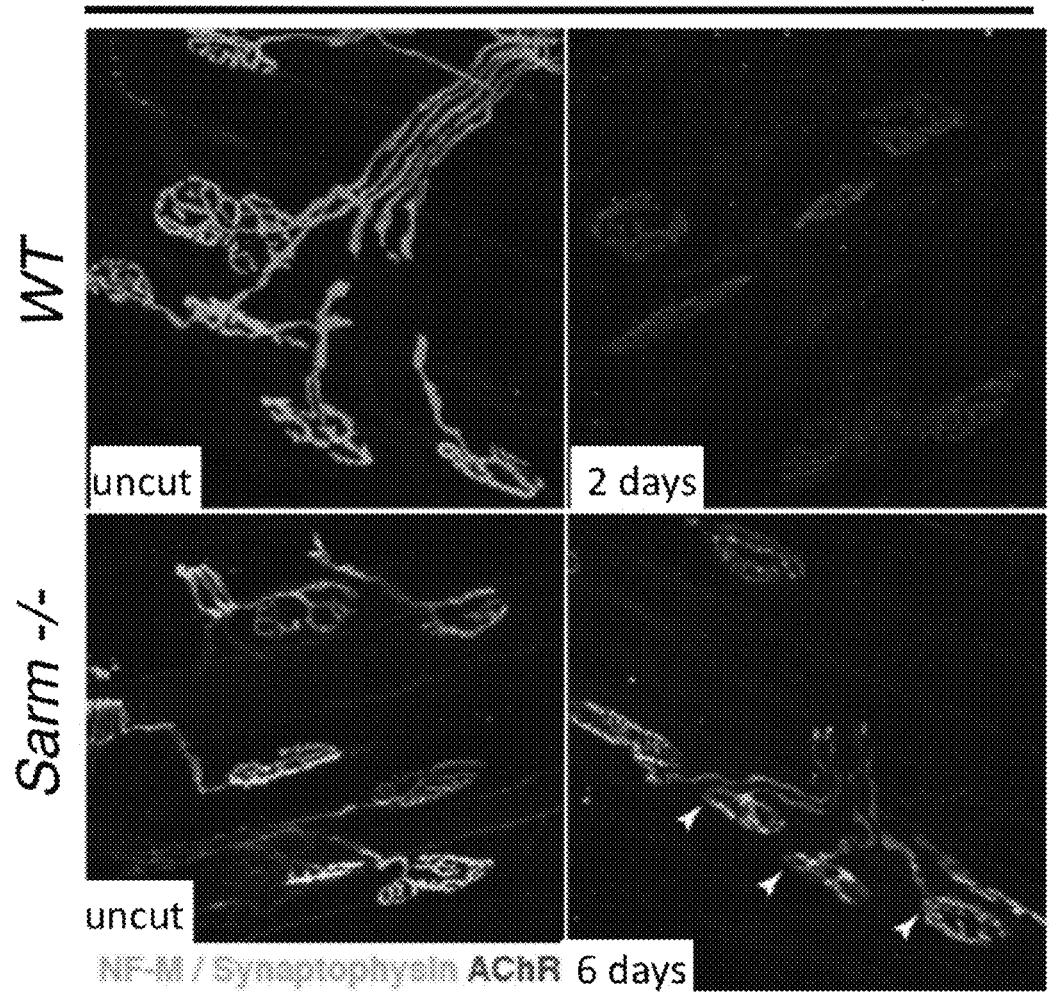
Figure 4D:
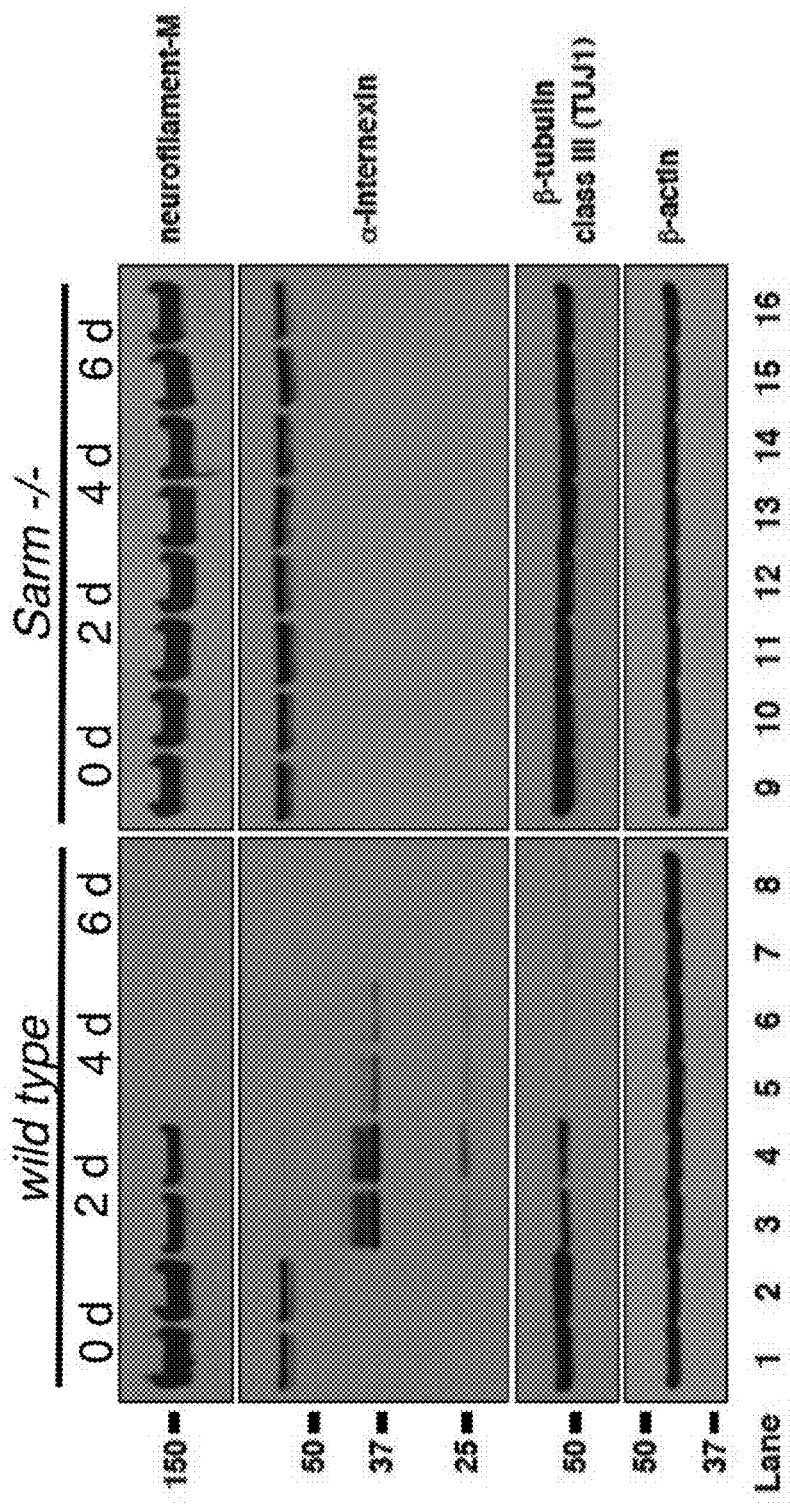
Figure 4E:
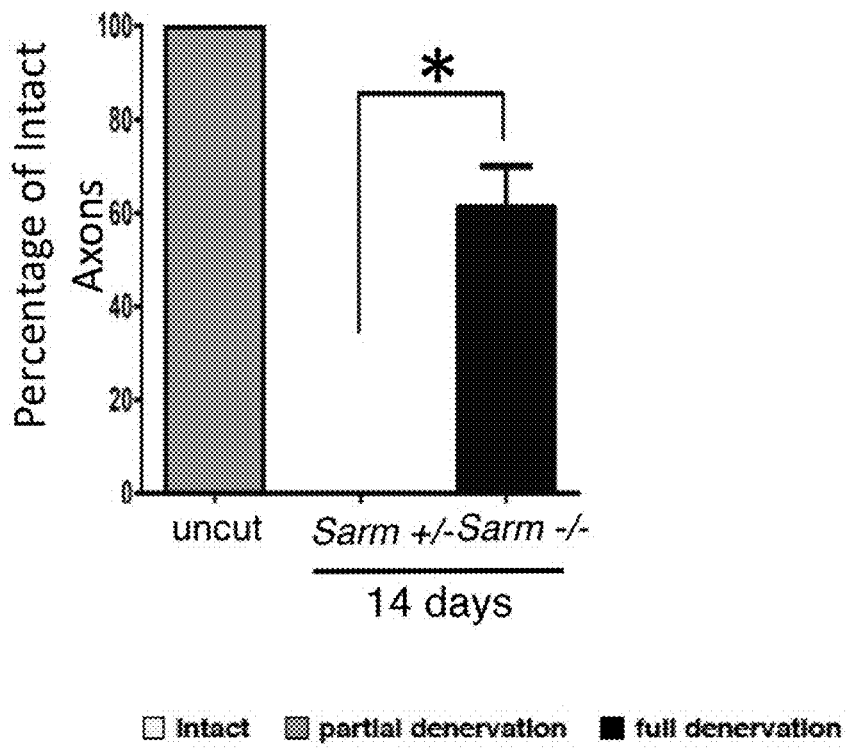
Figure 4F:
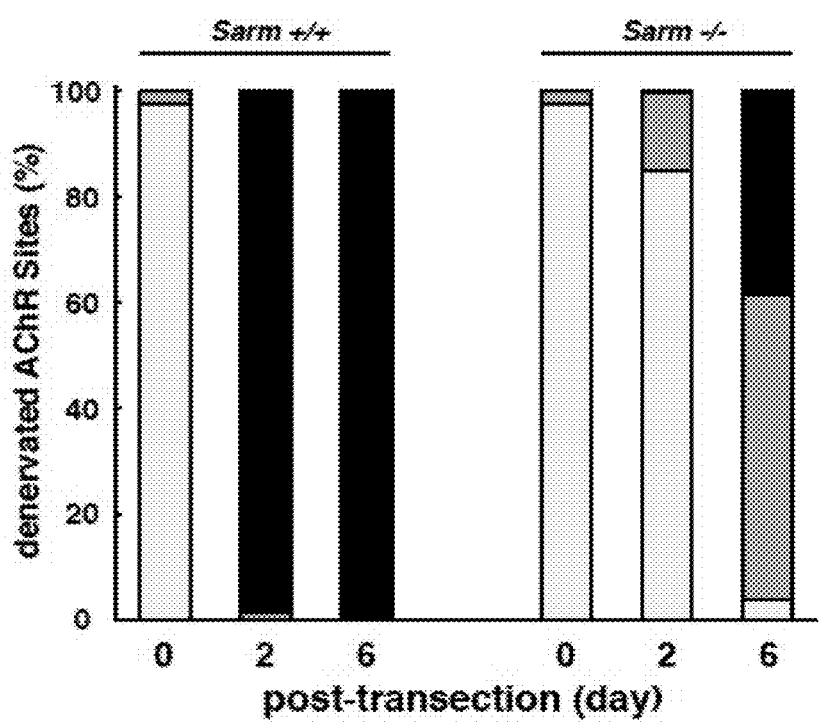

To test whether Sarm1 is required in vivo for Wallerian degeneration, sciatic nerve lesions of the right hind limb were performed in Sarm1−/− mice and their heterozygous littermate controls. Impressively, while Sarm1+/− controls exhibited a dramatic breakdown of the axon and myelin sheath within 3 days of injury, 61.2% of lesioned Sarm1−/− axons were protected from degeneration at least 14 days after injury (p=0.002) (FIG. 4A,E). Analysis of sciatic nerve ultrastructure revealed a remarkable structural preservation at 14 days after axotomy of the Schwann cell and myelin sheath, axonal neurofilaments, and axonal mitochondria (FIG. 4B; FIG. 6A). Western blots of sciatic nerve were performed and probed with antibodies to neurofilament-M (NF-M), α-Internexin, and β-tubulin class III (TUJI). While a dramatic breakdown of these proteins was observed in wild type nerves, they remained largely intact in Sarm1−/− axons (FIG. 4D). In addition, preservation of the NF-M signal was observed by immunofluorescent staining of the nerve in Sarm1 mutants (FIG. 6A).

Neuromuscular junctions were examined in tibialis anterior muscles after sciatic nerve transection. Synaptic integrity was scored by co-localization of presynaptic marker (NF-M/synaptophysin) with the post-synaptic acetylcholine receptor (AChR). In wild type animals, motor endplate denervation was complete by 2 days after axotomy. However in Sarm1−/− animals, most synaptic terminals were partially innervated even at 6 days after injury (FIG. 4C,F). Macrophage/monocyte infiltration of lesioned nerves was suppressed in Sarm1 knockout animals (FIG. 6B). Taken together, these results indicate that Sarm1−/− mutations provide a dramatic preservation of sciatic nerves in vivo from initial axonal cytoskeletal breakdown to recruitment of macrophages for myelin clearance.

Finally, in vivo localization of dSarm and Sarm1 was assayed. To determine the subcellular localization of dSarm, a GFP-tagged version of dSarm (UAS-dSarm-GFP) was generated and expressed via tdc-Gal4 in larval motorneurons. dSarm-GFP localization was assayed in third instar larvae. Axons and cell bodies were identified by co-expression of UAS-mCD-mCherry. Expression of dSarm::GFP in larval neurons resulted in punctate localization in neuronal cell bodies, and broad localization to neurites. Similarly, immunostaining with anti-Sarm1 antibodies of in vitro cultured mammalian neurons showed a broad, punctate pattern in neurites, and endogenous Sarm1 did not show preferential localization with a mitochondrial marker.

REFERENCES CITED

1. A. Waller, Philos. Trans. R. Soc. Lond. B Biol. Sci. 140, 423 (1850).
2. E. R. Lunn, V. H. Perry, M. C. Brown, H. Rosen, S. Gordon, Eur J Neurosci 1, 27 (1989).
3. J. D. Glass, T. M. Brushart, E. B. George, J. W. Griffin, J Neurocytol 22, 311 (May, 1993).
4. M. C. Raff, A. V. Whitmore, J. T. Finn, Science 296, 868 (May 3, 2002).
5. M. P. Coleman, V. H. Perry, Trends Neurosci 25, 532 (October, 2002).
6. T. G. Mack et al., Nat Neurosci 4, 1199 (December, 2001).
7. M. P. Coleman, M. R. Freeman, Annu Rev Neurosci 33, 245 (2010).
8. T. L. Deckwerth, E. M. Johnson, Jr., Dev Biol 165, 63 (September, 1994).
9. J. T. Finn et al., J Neurosci 20, 1333 (Feb. 15, 2000).
10. A. V. Whitmore, T. Lindsten, M. C. Raff, C. B. Thompson, Cell Death Differ 10, 260 (February, 2003).
11. Q. Zhai et al., Neuron 39, 217 (Jul. 17, 2003).
12. E. D. Hoopfer et al., Neuron 50, 883 (Jun. 15, 2006).
13. B. R. Miller et al., Nat Neurosci 12, 387 (April, 2009).
14. T. Lee, L. Luo, Trends Neurosci 24, 251 (May, 2001).
15. L. Luo, D. D. O'Leary, Annu Rev Neurosci 28, 127 (2005).
16. I. Miguel-Aliaga, S. Thor, Development 131, 6093 (December, 2004).
17. M. E. Grether, J. M. Abrams, J. Agapite, K. White, H. Steller, Genes Dev 9, 1694 (Jul. 15, 1995).
18. B. L. MacInnis, R. B. Campenot, Mol Cell Neurosci 28, 430 (March, 2005).
19. R. R. Buss, W. Sun, R. W. Oppenheim, Annu Rev Neurosci 29, 1 (2006).
20. M. Mink, B. Fogelgren, K. Olszewski, P. Maroy, K. Csiszar, Genomics 74, 234 (Jun. 1, 2001).
21. Y. Kim et al., J Exp Med 204, 2063 (Sep. 3, 2007).
22. C. F. Chuang, C. I. Bargmann, Genes Dev 19, 270 (Jan. 15, 2005).
23. C. Chang, Y. W. Hsieh, B. J. Lesch, C. I. Bargmann, C. F. Chuang, Development 138, 3509 (August, 2011).
24. E. B. George, J. D. Glass, J. W. Griffin, J Neurosci 15, 6445 (October, 1995).
25. S. A. Barrientos et al., J Neurosci 31, 966 (Jan. 19, 2011).
26. J. M. MacDonald et al., Neuron 50, 869 (Jun. 15, 2006).
27. M. A. Avery, A. E. Sheehan, K. S. Kerr, J. Wang, M. R. Freeman, J Cell Biol 184, 501 (Feb. 23, 2009).
28. T. Klein, Methods Mol Biol 420, 253 (2008).
29. N. H. Patel, Methods Cell Biol 44, 445 (1994).
30. A. Nikolaev, T. McLaughlin, D. D. O'Leary, M. Tessier-Lavigne, Nature 457, 981 (Feb. 19, 2009).
31. J. Gilley, M. P. Coleman, PLoS Biol 8, e1000300 (January, 2010).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing axonal or synaptic degradation in a neuron, the method comprising:
   selecting a neuron with or at an increased risk for developing axonal or synaptic degradation; and
   contacting the neuron with an effective amount of a composition comprising a small interfering RNA (siRNA) that binds to sterile α/Armadillo/Toll-Interleukin receptor homology domain protein (SARM) mRNA for a time sufficient to inhibit SARM expression, thereby reducing axonal or synaptic degradation in the neuron.

2. The method of claim 1, wherein the siRNA binds to SARM mRNA comprising a nucleic acid sequence selected from the group consisting of SEQ ID NO: 1, 3 and 5.

3. A method for reducing axonal or synaptic degradation in a subject with or at risk for developing axonal or synaptic degradation, the method comprising:
   selecting a subject with or at an increased risk for developing axonal or synaptic degradation; and
   treating the subject with an effective amount of a composition comprising a siRNA compound that binds to SARM mRNA for a time sufficient to inhibit SARM expression, thereby reducing axonal or synaptic degradation in the subject.

4. The method of claim 3, wherein the subject at an increased risk for developing axonal or synaptic degradation is a subject that has experienced trauma of the CNS or PNS but that does not present symptoms of neurodegenerative disease.

5. The method of claim 3, wherein the subject at an increased risk for developing axonal or synaptic degradation is a subject with diabetes but without diabetic neuropathy.

6. The method of claim 3, wherein the subject at an increased risk for developing axonal or synaptic degradation is a subject scheduled to be exposed to a chemotherapeutic agent associated with the onset and/or development of neurodegeneration.

7. The method of claim 3, wherein the subject at an increased risk for developing axonal or synaptic degradation is a subject scheduled to undergo or undergoing chemotherapy, or treatment with a toxin associated with neurodegeneration.

8. The method of claim 3, wherein the subject has or is at an increased risk of neurodegenerative disease.

9. The method of claim 3 or 8, wherein the axonal or synaptic degradation is in the central nervous system (CNS) or the peripheral nervous system (PNS).

10. The method of claim 9, wherein the axonal or synaptic degradation is in the PNS.

\* \* \* \* \*

UNITED STATES PATENT AND TRADEMARK OFFICE
CERTIFICATE OF CORRECTION

PATENT NO. : 9,486,521 B2
APPLICATION NO. : 14/087206
DATED : November 8, 2016
INVENTOR(S) : Marc Freeman and Stephan Zuchner Page 1 of 1

It is certified that error appears in the above-identified patent and that said Letters Patent is hereby corrected as shown below:

In the Specification

Column 1, Lines 16-19, delete:
"FEDERALLY SPONSORED RESEARCH OR DEVELOPMENT
This invention was made with Government support under Grant Nos. R01 NS059991, U54NS065712, and R01NS072248, awarded by the National Institutes of Health. The Government has certain rights in the invention."

And insert:
--STATEMENT OF FEDERALLY SPONSORED RESEARCH
This invention was made with government support under Grant numbers NS059991, NS065712, NS052767 and NS054132 awarded by the National Institutes of Health. The Government has certain rights in the invention.--

Signed and Sealed this
Fourth Day of July, 2017

Joseph Matal
*Performing the Functions and Duties of the*
*Under Secretary of Commerce for Intellectual Property and*
*Director of the United States Patent and Trademark Office*